US012595342B2

(12) United States Patent
Chausson et al.

(10) Patent No.: US 12,595,342 B2
(45) Date of Patent: Apr. 7, 2026

(54) CHITOSAN-BASED BEADS, AND PREPARATION, COMPOSITIONS AND USES THEREOF

(71) Applicant: KIOMED PHARMA, Herstal (BE)

(72) Inventors: Mickaël Chausson, Huy (BE); Sandrine Emilia Gautier, Liege (BE); Laurence Hermitte, Bouc Bel Air (FR); Antoine Rabeux, Huy (BE); Guillermo Rocasalbas, Liege (BE)

(73) Assignee: KIOMED PHARMA, Herstal (BE)

( * ) Notice: Subject to any disclaimer, the term of this patent is extended or adjusted under 35 U.S.C. 154(b) by 817 days.

(21) Appl. No.: 17/790,180

(22) PCT Filed: Nov. 22, 2021

(86) PCT No.: PCT/EP2021/082454
§ 371 (c)(1),
(2) Date: Jun. 30, 2022

(87) PCT Pub. No.: WO2022/106676
PCT Pub. Date: May 27, 2022

(65) Prior Publication Data
US 2023/0066712 A1    Mar. 2, 2023

(30) Foreign Application Priority Data
Nov. 23, 2020    (FR) ...................................... 2012010

(51) Int. Cl.
| | |
|---|---|
| *C08J 3/075* | (2006.01) |
| *A61L 27/48* | (2006.01) |
| *A61L 27/52* | (2006.01) |
| *C08B 37/08* | (2006.01) |
| *C08J 3/24* | (2006.01) |

(52) U.S. Cl.
CPC .............. *C08J 3/075* (2013.01); *A61L 27/48* (2013.01); *A61L 27/52* (2013.01); *C08B 37/003* (2013.01); *C08B 37/0072* (2013.01); *C08J 3/24* (2013.01); *A61L 2400/06* (2013.01); *A61L 2430/34* (2013.01); *C08J 2305/08* (2013.01)

(58) Field of Classification Search
CPC ....... C08L 5/08; A61K 31/722; A61K 9/0019; C08J 3/075
See application file for complete search history.

(56) References Cited

U.S. PATENT DOCUMENTS

| | | | | |
|---|---|---|---|---|
| 6,660,301 B1 * | 12/2003 | Vogel | ................ | A61K 47/6927 |
| | | | | 514/777 |
| 10,612,001 B2 | 4/2020 | Hazot et al. | | |
| 2013/0171126 A1 * | 7/2013 | Letourneur | .......... | A61K 9/0019 |
| | | | | 424/602 |
| 2019/0046429 A1 * | 2/2019 | Khoshbin | ............ | A61K 31/381 |

FOREIGN PATENT DOCUMENTS

| | | | |
|---|---|---|---|
| CN | 102688195 A | 9/2012 | |
| CN | 103937014 A | 7/2014 | |
| CN | 107325306 A | 11/2017 | |
| JP | 2007516333 A | 6/2007 | |
| JP | 62-70401 B2 | 1/2018 | |
| WO | 2016016463 A1 | 2/2016 | |
| WO | 2016087762 A1 | 6/2016 | |
| WO | 2019105718 A1 | 6/2019 | |
| WO | WO-2019105719 A1 * | 6/2019 | ............. A61Q 19/08 |

OTHER PUBLICATIONS

Luo Yangchao et al (Food Hydrocolloids, 2013, vol. 31, pp. 332-339) (Year: 2013).*
Ahmadi et al (Research in Pharmaceutical Sciences, Feb. 2015, vol. 10, pp. 1-16) (Year: 2015).*
WO-2019105719-A1 (Google English translation, downloaded Jun. 2025) (Year: 2025).*
Chen et al, "Synthesis and pH Sensitivity of Carboxymethyl Chitosan-Based Polyampholyte Hydrogels for Protein Carrier Matrices", Biomaterials, 2004, pp. 3725-3732, vol. 25.
Xu et al., "Carboxymethyl Chitosan/Gelatin/Hyaluronic Acid Blended-Membranes as Epithelia Transplating Scaffold for Corneal Wound Healing", Carbohydrate Polymers, 2018, pp. 240-250, vol. 192.
Anitha et al., "Synthesis, Characterization, Cytotoxicity and Anti-bacterial Studies of Chitosan, O-Carboxymethyl and N,O-Carboxymethyl Chitosan Nanoparticles", Carbohydrate Polymers, 2009, pp. 672-677, vol. 78.
Bergeret-Galley "Comparison of Resorable Soft Tissue Fillers", Aesthetic Surgery Journal, Jan./Feb. 2004, pp. 33-46, vol. 24, No. 1.
Chen et al., "A Novel pH-Sensitive Hydrogel Composed of N,O-Carboxymethyl Chitosan and Alginate Cross-Linked by Genipin for Protein Drug Delivery", Journal of Controlled Release, 2004, pp. 285-300, vol. 96, No. 2.
Chen et al., "Carboxymethyl-Chitosan Protects Rabbit Chondrocytes from Interleukin-1b-Induced Apoptosis", European Journal of Pharmacology, 2006, pp. 1-8, vol. 541.
Czechowska-Biskup et al., "Synthesis of Chitosan and Carboxymethyl Chitosan Hydrogels by Electron Beam Irradiation", Progress on Chemistry and Application of Chitin and its Derivatives, 2016, pp. 27-45, vol. 21.
Deng et al., "Injectable in situ Cross-Linking Chitosan-Hyaluronic Acid Based Hydrogels for Abdominal Tissue Regeneration", Scientific Reports, 2017, pp. 1-13, vol. 7, No. 2699.

(Continued)

*Primary Examiner* — Mark V Stevens
(74) *Attorney, Agent, or Firm* — Thompson Coburn LLP; Steven M. Ritchey

(57) ABSTRACT

The invention relates to beads and a composition comprising an aqueous phase comprising a plurality of beads, the beads comprising or consisting in a hydrogel matrix comprising at least one carboxyalkyl chitosan having glucosamine units, N-acetyl-glucosamine units and glucosamine units substituted with a carboxyalkyl group, the carboxyalkyl chitosan being crosslinked by covalent bonds between the carboxyalkyl chitosan chains and/or co-crosslinked by covalent bonds with one or more other polymers.
The invention also relates to processes for their preparation and applications thereof.

41 Claims, No Drawings

(56)  References Cited

OTHER PUBLICATIONS

Dergunova, et al., "Characterization of Novel Chemically Modified Fungal Polysaccharides as the Macrophage Stimulators", International Immunopharmacology, 2009, pp. 729-733, vol. 9.

Di Mario et al., "Chitin and Chitosan from Basidiomycetes", International Journal of Biological Macromolecules, 2008, pp. 8-12, vol. 43.

Fonseca-Santos et al., "An Overview of Carboxymethyl Derivatives of Chitosan: Their Use as Biomaterials and Drug Delivery Systems", Materials Science and Engineering C, 2017, pp. 1349-1362, vol. 77.

Huang et al., "Injectable Nano-Hydroxyapatite (n-HA)/Glycol Chitosan (G-CS)/Hyaluronic Acid (HyA) Composite Hydrogel for Bone Tissue Engineering", Royal Society of Chemistry, 2016, pp. 1-22.

Kaderli et al., "A Novel Biocompatible Hyaluronic Acid-Chitosan Hybrid Hydrogel for Osteoarthrosis Therapy", International Journal of Pharmaceutics, 2015, pp. 158-168, vol. 483.

Liu et al., "Thermosensitive Injectable In-Situ Forming Carboxymethyl Chitin Hydrogel for Three-Dimensional Cell Culture", Acta Biomaterialia, 2016, pp. 228-237, vol. 35.

Luo et al., "Development of carboxymethyl chitosan hydrogel beads in alcohol-aqueous binary solvent for nutrient delivery applications", Food Hydrocolloids, 2013, pp. 332-339, vol. 31, No. 2.

Mi et al., "In vivo biocompatibility and degradability of a novel injectable-chitosan-based implant", Biomaterials, 2002, pp. 181-191, vol. 23, No. 1.

Micheels et al., "Effect of Different Crosslinking Technologies on Hyaluronic Acid Behavior: A Visual and Microscopic Study of Seven Hyaluronic Acid Gels", Journal of Drugs in Dermatology, May 2016, pp. 600-608, vol. 15, No. 5.

Ngo et al., "Antioxidant Effects of Chitin, Chitosan, and Their Derivatives", Advances in Food and Nutrition Research, 2014, pp. 15-31, vol. 73.

Poon et al., "Cytocompatible Hydroge is Based on Photocrosslinkable Methacrylated O'Carboxymethylchitosan with Tunable Charge: Snythesis and Characterization", Adv. Funct. Mater., 2007, pp. 2139-2150, vol. 17.

Rufato et al., "Hydrogels Based on Chitosan and Chitosan Derivatives for Biomedical Applications", IntechOpen, 2018, pp. 1-40.

Skorik et al., "Evaluation of Various Chitin-Glucan Derivatives from Aspergillus Niger as Transition Metal Adsorbents", Bioresource Technology, 2010, pp. 1769-1775, vol. 101.

So, "Improving Patient Compliance with Biopharmaceuticals by Reducing Injection-Associated Pain", J Mucopolysacch Rare Dis, 2015, pp. 15-18, vol. 1.

Song et al., "Peritoneal Adhesion Prevention with a Biodegradable and Injectable N, O-Carboxymethyl Chitosan-Aldehyde Hyaluronic Acid Hydrogel in a Rat Repeated-Injury Model", Scientific Reports, 2016, pp. 1-13, vol. 6, No. 37600.

Jjang et al., "The Development, Characterization and Application of Water Soluble Chitosan", 2011, IntechOpen, pp. 109-130.

Upadhyaya et al., "The Implications of Recent Advances in Carboxymethyl Chitosan Based Targeted Drug Delivery and Tissue Engineering Applications", Journal of Controlled Release, 2014, pp. 54-87, vol. 186.

Valyova et al., "Evaluation of in vitro Antioxidant Activity and Free Radical Scavenging Potential of Variety of Tagetes Erecta L. Flowers Growing in Bulgaria", International Journal of Applied Research in Natural Products, 2012, pp. 19-25, vol. 5, No. 2.

Waller et al., "Preventing Friction Induced Chondrocyte Apoptosis: A Comparison of Human Synovial Fluid and Hylan G-F 20", The Journal of Rheumatology, Jul. 2012, pp. 1473-1480, vol. 39, No. 7.

Yang et al., "Ophthalmic Drug-Loaded N,O-Carboxymethyl Chitosan Hydrogels: Synthesis, In Vitro and In Vivo Evaluation", Acta Pharmacologica Sinica, 2010, pp. 1625-1634, vol. 31, No. 12.

Zamani, "Superabsorbent Polymers from the Cell Wall of Zygomycetes Fungi", Department of Chemical and Biological Engineering, Chalmers University of Technology, 2010, pp. 1-68.

Wang et al., "Preparation of temperature and pH-sensitive carboxymethyl chitosan/sodium alginate hydrogel microsphere", Applied Chemical Industry, Aug. 2015, pp. 1464-1467, vol. 44, No. 8.

Jaidee et al "1H-N M R analysis of degree of substitution in N, O-carboxymethyl chitosans from various chitosan sources and types." Advanced Materials Research, 2012, No. 506 pp. 158-161.

Zhao et al "Biochemical activities of N, O-carboxymethyl chitosan from squid cartilage" Carbohydrate polymers, 2011, No. 85 vol. 4, pp. 832-837.

* cited by examiner

CHITOSAN-BASED BEADS, AND PREPARATION, COMPOSITIONS AND USES THEREOF

CROSS-REFERENCE TO RELATED APPLICATIONS

This application is a U.S. National Phase application of PCT/EP2021/082454, filed on Nov. 22, 2021, claiming the benefit of French Application No. 2012010, filed on Nov. 23, 2020, both of which are incorporated herein by reference in their entireties.

This invention relates to administrable, and in particular injectable, implantable or instillable, beads in a human being or an animal, comprising or consisting of a hydrogel matrix comprising at least one crosslinked carboxyalkyl chitosan. This invention relates to administrable, and in particular injectable, implantable or instillable, compositions in a human being or an animal, comprising beads or consisting in a hydrogel matrix comprising at least one crosslinked carboxyalkyl chitosan.

This invention also relates to a method for preparing these beads, compositions, particularly in the form of suspension or dispersion, comprising them, as well as their applications particularly their applications by administration in a human being or an animal, particularly by injection through a needle for injection or an endoscopic system, by implantation, by instillation or any other path adapted to the target indication.

This invention more particularly relates to beads administrable to a human being or an animal comprising or consisting of a hydrogel matrix comprising at least one carboxyalkyl chitosan crosslinked by covalent bonds, the compositions comprising them, their manufacturing process and their different applications, in particular in the therapeutic, rheumatologic, orthopaedic, ophthalmologic, cosmetic medicine, plastic surgery, internal surgery, dermatology, gynaecology or cosmetic field.

STATE OF THE ART

Products administrable to human beings or animals made of bioresorbable polymer particles are already marketed, particularly for volumisation indications of skin tissue for cosmetic purposes and medication delivery indications, by injection. However, these products call for improvement, particularly in terms of tolerance, biointegration and volumising effect.

It has now been recognised that the body's response facing particle systems administrated in a tissue depends on several parameters, particularly composition, shape, size, biodegradability, surface.

Thus, there are commercial products based on bioresorbable beads which are not in the form of hydrogel, but present risks of inducing responses to foreign bodies and granulomas. Therefore, they are limited to a usage localised to deep tissue layers and, for example, they cannot be administrated in the dermis. Such microspheres can be injected by intraocular path (Sustained treatment of retinal vascular diseases with self-aggregating sunitinib microparticles, Nature Comm 11, 694, 2020).

In addition, the beads according to the invention should be suitable for use in human beings or animals, particularly in terms of cohesion, safety, immunocompatibility, bioresorbability, biomechanical properties, ease of administration and life or activity time. Yet the compositions of the state of the art do not offer such properties satisfactorily and would be thus not in accordance with the present invention.

There are particular filling products obtained by extrusion of hydrogel formed by a matrix of crosslinked hyaluronic acid (HA). However, the shape obtained by extrusion is non-spherical and irregular, which results in a risk of response to a foreign material and granuloma usually higher than with a spherical shape, as described among others by Lemperle (Biocompatibility of injectable microspheres, Biomed J Sci Tech Res 2, 1, 2018). It is also known that the hydrogel beads obtained by extrusion require a larger force for injection through a thin needle than spherical hydrogel beads. It is recommended to use spherical shape hydrogel beads to favour proper short- and long-term tolerance and easy injection through thin needles.

There are in literature and particularly patent applications, spherical hydrogel beads of bioresorbable polymer(s) formed by crosslinking via non-covalent bonds. For example, international application WO 2011089173 (Biopharmex) describes an injectable composition for tissue filling of soft tissues. More particularly, this application describes a suspension of microspheres with an average volume diameter between 5 and 50 micrometres, said microspheres comprising 50 to 90% weight of at least one bioresorbable polysaccharide with respect to the total weight of microspheres, said microspheres inducing a second filling by tissue induction and containing at least one second bioresorbable polymer. These hydrogel microspheres offer poor stability due to the lack of covalent bonds; their integrity under their initial shape and size will thus be shortened after injection or implantation. Their suspension storage stability shall also be of short time.

There are other documents, describing the preparation of bioresorbable polymer hydrogel beads obtained by crosslinking through covalent bonds, such as for example the publication by Luo et al. which relates to carboxymethyl chitosan in the form of dehydrated beads (Development of carboxymethyl chitosan hydrogel beads in alcohol-aqueous binary solvent for nutrient delivery applications, Food Hydrocolloids 31, 332, 2013). However, Luo et al. used the crosslinking agent glutaraldehyde, which is not acceptable for injection in humans or animals. More particularly, Luo et al. describe none of the following properties: mechanical strength, elasticity, volumisation, immunocompatibility, injectability via a needle, ability to remove residues (salt and crosslinking agent) by the washing step without damaging the beads. But most of all, the inventors discovered that the method of Luo et al. is not suitable for the preparation of hydrogel beads starting with strongly substituted and/or acetylated chitosan derivatives and with the crosslinking agent BDDE (preferred to the glutaraldehyde). In addition, the chitosan derivative used by Luo et al. has a degree of acetylation and a degree of substitution not allowing to provide acceptable immunoreactivity. It is thus not possible for the skilled person to learn satisfactorily from this document to develop the beads according to the present invention.

Thus, no injectable beads exist meeting satisfactorily the goals set by the inventors. The field of preparation of the hydrogel beads based on bioresorbable polymers, spherical, easily administrable, particularly by injection and perfectly tolerated is complex and research is still underdeveloped on this matter. The inventors thus sought to develop this technology yet poorly explored.

PURPOSES OF THE INVENTION

One purpose of the present invention is to solve the technical problem of providing injectable beads with proper tolerance for the targeted indications after administration in humans or animals, particularly by injection or implantation, more particularly in the therapeutic, surgical and cosmetic fields.

One purpose of the present invention is to solve the technical problem of providing such injectable beads for volumisation indications (for example volumising/remodelling effect of the outline of the face/body in cosmetic medicine or to treat lipoatrophies) or drug delivery.

Especially, one purpose of the present invention is to solve the technical problem of providing bioresorbable beads, adapted to use in contact with a tissue from humans or animals, acceptable in terms of biomechanical properties, lifetime or in situ activity, search for proper health safety, including acceptable short- and long-term immunological reaction and/or reaction to foreign bodies, and offering beneficial effects, particularly in the context of regenerative or anti-age medicine, for example in the therapeutic, rheumatologic, orthopaedic, gynaecologic, ophthalmologic, cosmetic medicine, plastic surgery, internal surgery, dermatologic or cosmetic field.

One purpose of the present invention is to solve the technical problem of providing such injectable beads presenting satisfactory stability during their storage and appropriate to the targeted indication.

Especially, one purpose of the present invention is to solve the technical problem of providing such injectable beads offering satisfactory tolerance, physico-chemical properties and volumising effect and for a duration sufficient after subcutaneous implantation.

One purpose of the present invention is to solve the technical problem of providing beads with modular properties according to the targeted indication.

Especially, one purpose of the present invention is to solve the technical problem of providing beads which resist purification steps by washing in aqueous environments in order to remove undesirable residues from the process and balance the pH and osmolality of the beads with those of a physiological medium.

One purpose of the present invention is also to solve the technical problem of providing bioresorbable injectable beads having a sustained effect over time, particularly in terms of volumising effect and/or delivery of at least one compound of interest for the targeted indication (therapeutic active ingredient, nutrient, etc.)

One purpose of the present invention is also to solve the technical problem of providing (injectable) beads with an essentially spherical shape and a smooth, non-rough surface.

Especially, one purpose of the present invention is to solve the technical issue of providing such beads with satisfactory injection facility when intended for the delivery by injection, without altering integrity of the beads at the outlet of the injection system.

One purpose of the present invention is also to solve the technical problem of providing beads suspendable in an aqueous phase and remaining integral during their storage in such a suspension.

One purpose of the present invention is also to solve the technical problem of providing beads suspendable in an aqueous phase and remaining integral during their sterilisation in such a suspension, in particular by a wet heat sterilisation process.

One purpose of the present invention is to solve the technical problems listed above by providing chitosan derivative beads.

DESCRIPTION OF THE INVENTION

To provide beads injectable in humans or animals, these should be biocompatible with the tissues into which they are injected or implanted. Preferably, to provide biocompatible beads, it is preferred they comprise a polymeric, preferably biopolymeric matrix, which is non-toxic and non-immunoreactive. The polymers of the bead matrix according to the invention are advantageously bioresorbable and are neither toxic nor immunoreactive. Carboxyalkyl chitosan derivatives described in the PCT/EP2018/080763 and PCT/EP2018/080767 applications to KIOMED PHARMA are preferred, as they withstand well that the matrixes are not toxic, or immunoreactive. Indeed, any chitosan derivative cannot be used to form hydrogels acceptable for use in humans or animals, particularly in terms of immunocompatibility (or immunoreactivity). By immunocompatibility, it is meant any substance foreign to the human body or other living organisms which would not stimulate the cells or the immune system resulting in a specific immune response with antigen. PCT/EP2020/064159 application relates to the use of hydrogel matrixes prepared by crosslinking such chitosan derivatives. It had been contemplated for some time to use a matrix of such a crosslinked chitosan derivative according to this PCT/EP2020/064159 international application to prepare beads meeting the objectives of the present invention. However, to prepare beads from these crosslinked chitosan derivative matrixes, it is for example necessary to extrude or mill the hydrogel. Yet, the inventors found that such beads were not satisfactory as their shape is non-spherical, non-regular (that is with angular parts, some surface roughness, a poorly controlled size distribution), which increases the risk of reaction to foreign material once injected or implanted in a tissue of a human or animal (Lemperle 2018, Biocompatibility of injectable microspheres, Biomed J Sci Tech Res 2, 1, 2018)). Likewise, they are not easy to inject due to their irregular shape.

Based on this observation, the inventors devised a research programme. More particularly they considered preparing the spherical hydrogel beads based on carboxyalkyl chitosan according to PCT/EP2018/080763 and PCT/EP2018/080767, by following the various methods described in the literature for the carboxyalkylated chitosan derivatives.

Thus, the methods of ionic crosslinking or forming polyelectronic complexes described for example by Anitha et al. (Synthesis, characterisation, cytotoxicity and antibacterial studies of chitosan, O-carboxymethyl and N,O-carboxymethyl chitosan nanoparticles, Carbohydrate Polymers 78, 672, 2009), Anitha et al. (Curcumin-loaded N,O-carboxymethyl chitosan nanoparticles for cancer drug delivery, J Biomater Sci 23, 1381, 2012), Lin and Lin (Preparation of N,O-carboxymethyl chitosan nanoparticles as an insulin carrier, 2009), Kalliola et al. (The pH-sensitive properties of carboxymethyl chitosan nanoparticles crosslinked with calcium ions, Colloids Surfaces B, 153, 229, 2017) and Feng et al. (Chitosan/O-carboxymethyl chitosan nanoparticles for efficient and safe oral anticancer drug delivery, Int J Pharma 457, 158, 2013) did not offer satisfactory results. Indeed, most of the time, hydrogel beads are not formed, that is the polymer precipitates in the spherical shape but is not stabilised and is not viscoelastic and hydrated as hydrogel beads are, or if they are formed, they do not remain integral once incorporated in a continuous phase, they are not stable.

It has been surprisingly discovered as a result of many developments made by the inventors that the present invention allows providing beads which are satisfactory and meet the purposes of the present invention.

The invention more particularly relates to a composition comprising an aqueous phase comprising a plurality of beads, the beads comprising or consisting of a hydrogel matrix comprising at least one carboxyalkyl chitosan having glucosamine units, N-acetyl-glucosamine units and glucosamine units substituted with a carboxyalkyl group, the carboxyalkyl chitosan being crosslinked by covalent bonds between the carboxyalkyl chitosan chains and/or co-crosslinked by covalent bonds with one or more other polymers.

The invention also relates to one or more injectable beads in humans or animals, the beads comprising or consisting of a hydrogel matrix comprising at least one carboxyalkyl chitosan having glucosamine units, N-acetyl-glucosamine units and glucosamine units substituted with a carboxyalkyl group, said carboxyalkyl chitosan having a degree of acetylation higher than 30% and up to 80%, expressed as the number of moles of N-acetyl groups with respect to the number of moles of total glucosamine units, said carboxyalkyl chitosan being crosslinked by covalent bonds between the carboxyalkyl chitosan chains and/or co-crosslinked by covalent bonds with one or more other polymers.

Carboxyalkyl Chitosan

It is known that advantageous chitosan derivatives such as carboxyalkyl chitosan described in the Kiomed Pharma patent applications filed under the numbers PCT/EP2018/080763 and PCT/EP2018/080767 and their family the contents of which is incorporated in the present invention by reference. In addition, the international application by Kiomed Pharma, PCT/EP2020/064159, the content of which is incorporated in the present invention by reference, describes carboxyalkyl chitosans, crosslinked, alone or crosslinked with another polymer, as a hyaluronan for example.

A matrix according to the present invention can be characterised by the starting carboxyalkyl chitosan, which is crosslinked and/or co-crosslinked with one or more polymers to form a matrix according to the invention.

According to a first aspect, a carboxyalkyl chitosan is used (fungal origin) having glucosamine units, N-acetyl-glucosamine units and glucosamine units substituted with a carboxyalkyl group, said carboxyalkyl chitosan having preferably a degree of substitution with a carboxyalkyl group higher than 20%, expressed in number of moles of the substituent with respect to the number of moles of total units.

This is also referred to as a chitosan or substituted chitosan derivative.

Carboxyalkyl chitosan is prepared by chitosan substitution. Typically, a carboxyalkyl chitosan is prepared according to the patent applications of Kiomed Pharma filed under the numbers PCT/EP2018/080763 and its family (particularly FR 17 61314 and EP 18799772.1) and PCT/EP2018/080767 and its family (particularly FR 17 61323 and EP 18799773.9), and PCT/EP2020/064159 and its family (particularly FR 19 05504) which are incorporated here by reference more particularly to illustrate the preparation of a carboxyalkyl chitosan.

For example, chitosan is referenced under CAS number 9012-76-4.

Chitosan used for the invention is advantageously of fungal origin, and preferably originates from the mycelium of a fungus of the Ascomycete type and especially *Aspergillus niger*, and/or a Basidiomycete fungus and especially *Lentinula edodes* (shiitake) and/or *Agaricus bisporus* (cultivated mushroom). Preferably, chitosan originates from *Agaricus bisporus*. Chitosan is preferably very pure, that is containing little impurity originating from its fungal origin or the manufacturing process, and of a microbiological quality compatible with its use as an implant or pharmaceutical composition. A chitosan preparation method is that described in patents WO 03/068824 (EP 1483299; U.S. Pat. No. 7,556,946).

Generally, chitin is put in aqueous suspension in the presence of sodium hydroxide, and then the medium is heated at high temperature for a time variable according to the molecular mass desired. Chitosan is then purified in an acid medium and precipitated in an alkaline medium, washed and dried.

Preferably, chitosan is of a grade sufficiently pure for pharmaceutical use.

Chitosan is advantageously purified and then preferably dried. After purification, the process of the invention can include a step of drying the carboxyalkyl chitosan, and then possibly crushing it to obtain a powder. For example chitosan can be dried by water evaporation, for example by a spray-drying (atomisation), fluidised bed, or vacuum or atmospheric pressure heat drying process or by freeze drying.

This chitosan can then be substituted to produce a carboxyalkyl chitosan as for example as described in the invention.

Such a carboxyalkyl chitosan is then used to prepare the beads according to the invention.

To simplify, the DA and DS are expressed according to the carboxyalkyl chitosan before formation of the beads.

The degree of acetylation (DA) of chitosan is determined as described for example in the patent applications WO 2017009335 and WO 2017009346 by potentiometric titration. The DA of the chitosan and carboxyalkylated chitosan can be measured by known methods for chitosan, as liquid phase proton NMR, solid phase carbon-13 NMR, infra-red spectrometry, UV-visible spectrometry.

According to one alternative, the carboxyalkyl chitosan has a degree of acetylation lower than 30%, for example from 5% to 30%, expressed as a number of moles of N-acetyl-glucosamine units with respect to the total unit moles.

Advantageously, the carboxyalkyl chitosan has a degree of acetylation between 30 and 80%, expressed as a number of moles of N-acetyl-glucosamine units with respect to the total unit moles. The degree of acetylation is expressed as a number of N-acetyl groups (of D-glucosamine units) with respect to the total number of units of glucosamine present in the chitosan (N-acetyl-D-glucosamine, substituted N-acetyl-D-glucosamine, D-glucosamine and substituted D-glucosamine).

Advantageously, the carboxyalkyl chitosan has a degree of acetylation between 30 and 75%, expressed as a number of N-acetyl groups with respect to the total number of glucosamine units.

According to one alternative, the degree of acetylation ranges from 35 to 50%.

According to one alternative, the degree of acetylation ranges from 40 to 60%.

According to one alternative, the degree of acetylation ranges from 50 to 75%.

The degree of acetylation of chitosan carboxalkyl can be determined by solid phase carbon-13 NMR or by liquid phase proton NMR. Carboxyalkyl chitosan has advantageously a controlled degree of acetylation. By «chitosan having a controlled degree of acetylation», it is meant a product with a degree of acetylation, that is the proportion of N-acetyl-glucosamine units, can be adjusted in a controlled manner, particularly by an acetylation reaction.

Preferably, carboxyalkyl chitosan is reacetylated.

According to one alternative, the carboxyalkyl chitosan preparation process according to the invention comprises preparing a chitosan of fungal origin, reacetylating the chitosan and carboxyalkylating the chitosan reacetylated. Thus, the invention relates to a reacetylated carboxyalkyl chitosan. More specially, the invention relates to an anionic carboxyalkyl chitosan.

According to one embodiment, chitosan can therefore be dissolved in an aqueous medium, preferably slightly acidified (for example pH 6). Acetic anhydride can be added to the chitosan solution in one or more operations. A basic agent as for example soda and/or urea is then added. An alkylating agent as for example sodium monochloroacetate (that is sodium salt of chloroacetic acid) or chloroacetic acid is then added. Then the substituted chitosan is purified, recovered and dried.

According to one alternative, the carboxyalkyl chitosan preparation process according to the invention comprises preparing a chitosan, carboxyalkylating the chitosan, and then reacetylating the carboxyalkylated chitosan. Advantageously, such a method allows precise control of the degree of acetylation of the final carboxyalkyl chitosan, and more particularly a high degree of acetylation, for example higher than 40% to be obtained. Thus, the invention relates to a chitosan reacetylated, and then carboxyalkylated or a reacetylated carboxyalkyl chitosan.

According to one alternative, the process for preparing the carboxyalkyl chitosan according to the invention comprises preparing a chitin of fungal origin, carboxyalkylating the chitin, and possibly reacetylating the carboxyalkylated chitin to obtain the carboxyalkyl chitosan according to the invention.

According to one alternative, the process for preparing the carboxyalkylated chitosan according to the invention comprises preparing a chitin of fungal origin, deacetylating the chitin, carboxyalkylating the chitin, and possibly reacetylating the carboxyalkylated chitin to obtain the carboxyalkyl chitosan according to the invention.

According to one alternative, the carboxyalkyl chitosan has an average molecular mass lower than 500,000.

According to one specific alternative, the substituted chitosan preferably has an average molecular mass from 50,000 to 400,000.

The average molecular mass is the molecular mass of carboxyalkyl chitosan before formation of beads and cross-linking. Preferably here, the average molecular mass is the average molecular mass in viscosity (Mv), calculated from inherent viscosity. This expression is usual for the skilled person. Inherent viscosity ($\eta$) is measured by capillary viscosimetry, with a capillary viscosimeter of the Ubbelohde type, according to the monography 2.2.9 method of the European Pharmacopeia. The flow time of the solution through an adapted capillary tube is measured (Lauda, for example the capillary tube Ubbelohde 510 01 with a diameter of 0.53 mm) using an automatic viscometer I-Visc (Lauda). To calculate the average viscosimetric mass of carboxyalkyl chitosan, the equation of Mark-Houwink ($\eta=K*Mv^{\alpha}$) is then applied, wherein:

Mv is the average molecular mass in viscosity of carboxyalkyl chitosan,
$\eta$ is the inherent viscosity of carboxyalkyl chitosan,
the constants K and $\alpha$ have a value of 0.0686 and 0.7638, respectively such as determined beforehand for (non-substituted) chitosan by steric exclusion chromatography with a MALLS detector.

Intrinsic viscosity of carboxylakyl chitosan can usually be expressed to assess its average molecular mass.

Chitosan can be hydrolysed to reduce its molecular mass.

Typically, in non-crosslinked carboxyalkyl chitosan, the glucosamine units are D-glucosamine units (D-glucosamine units, N-acetyl-D-glucosamine units and at least one of the D-glucosamine units and N-acetyl-D-glucosamine units being substituted).

According to one alternative, a substituted chitosan has a substitution of the D-glucosamine units only.

According to another alternative, a substituted chitosan has a substitution of the D-glucosamine and N-acetyl-D-glucosamine units simultaneously, and in which the carboxyalkyl group is covalently bonded, according to one alternative to the amine groups of the chitosan only, or according to another alternative to the amine and hydroxyl groups of chitosan simultaneously.

The substitution is generally only partial, all units being not necessarily substituted.

According to one embodiment, the degree of substitution of the D-glucosamine units expressed as a number of moles of D-glucosamine units with respect to the number of moles of total units (D-glucosamine and N-acetyl-D-glucosamine units, whether substituted or not) of the substituted chitosan, ranges from 30% to 250%.

According to one embodiment, said carboxyalkyl chitosan has a degree of substitution with a group of carboxyalkyl higher than 20%, for example higher than 50%, for example lower than 200%, expressed in number of moles of the substituent with respect to the number of moles of total units.

According to one embodiment, the degree of substitution with a group of carboxyalkyl higher than 50%, expressed in number of moles of the substituent with respect to the number of moles of total units.

According to one embodiment, the degree of substitution of the D-glucosamine units expressed as a number of moles of D-glucosamine units with respect to the number of moles of total units (D-glucosamine and N-acetyl-D-glucosamine units, whether substituted or not) of the substituted chitosan, ranges from 50% to 200%, and further preferably higher than 70%.

According to one embodiment, the degree of substitution with a group of carboxyalkyl lower than 80%, expressed in number of moles of the substituent with respect to the number of moles of total units.

Typically, substitution is made by covalent bonding.

According to one alternative, the carboxyalkyl chitosan is an N,O-carboxyalkyl chitosan. The proportion of units substituted with a carboxyalkyl group in O position (O3 and/or O6 of the glucosamine and/or N-acetyl-glucosamine units) and/or in N position (glucosamine units) varies. The degree of substitution can thus be higher than 100%. Advantageously, the degree of substitution (DS) and degree of acetylation (DA) of carboxyalkyl chitosan are measured by solid phase carbon-13 magnetic resonance spectrometry (NMR), using a Bruker Spectrometer (Avance III HD 400 MHz, fitted with a PH MAS VTN 400SB BL4 N-P/H probe). For example, the spectrum is recorded at room temperature, a relaxation time between 1 and 8 seconds, a number of scans between 64 and 512. The areas of the carbon signals are determined after deconvolution. The carbons considered are as follows: «acetyl CH3» (carbon of the methyl of the acetyl group of N-acetyl-glucosamine units, substituted or not), «Cx» (carbon in position x of glucosamine and N-acetyl-glucosamine units, x ranging from 1 to 6) and «C=O» (carbon of the carbonyl of the carboxyalkyl substituent and carbon of the carbonyl C=O of the acetyl group of the N-acetyl-glucosamine units, substituted or not). To determine the DS of a given carboxyalkyl chitosan, the NMR spectrum of the carbon 13 of the precursor chitosan of this carboxyalkyl chitosan has also to be recorded. From the spectrum of the precursor chitosan, the «CSU ratio», that is the ratio of the area of the signal of the «CH3 acetyl» group (carbon of the methyl of the acetyl group of the N-acetyl-glucosamine units) to the area of the signal of the «C=O» (carbonyl carbon of the acetyl group of the N-acetyl-D-glucosamine units) is calculated. The DA of the carboxyalkyl chitosan is calculated according to the Formula 1, and the DS according to the Formula 2, where I represents the area of the signal of the carbon considered.

[Math 1]

$$DA = \frac{I_{CH3acetyl}}{\sum I_{Cx}/6}$$
Formula 1

[Math 2]

$$DS = \frac{I_{C=O} - I_{CH3acetyl/ratio\,CsU}}{\sum I_{Cx}/6}$$
Formula 2

Preferably, the ranges of degrees of substitution (DS) are expressed in connection with the result of solid phase carbon-13 NMR analysis in this description, since it is easily implemented.

The DA and DS can also be determined using other known methods for carboxyalkyl chitosans, for example by aqueous medium proton NMR, using a magnetic resonance spectrometer, for example according to the method described by Liu et al. (Carb Polym 137, 600, 2016), for example by adding a solution of deuterated hydrochloric acid thereto.

If another NMR method is more advantageous to estimate the DA and/or DS in a reliable manner, such a method should be used. The above methods should be adapted by the skilled person in terms of sample preparation and signals to be integrated, particularly according to the resolution, robustness and position of the protons of the signals to be used for calculating the degree of substitution.

The degree of carboxyalkylation (DS) of chitosan may advantageously range from 20 to 250%, preferably from 50 to 200%, and for example from 70 to 170%, expressed as the number of carboxyalkyl moles with respect of the number of moles of total units.

According to one alternative, the degree of carboxyalkylation (DS) of chitosan can advantageously range from 40 to 130%, and for example from 70 to 130%, expressed as the number of carboxyalkyl moles with respect of the number of moles of total units.

The degree of substitution of chitosan is typically correlated to the amount of reagents with respect to the chitosan starting from the reaction. As carboxyalkylating agents, mention can be made of acid chlorides (or their salts, for example sodium monochloroacetate), as for example those carrying one or more carboxymethyl, carboxyethyl, carboxypropyl, carboxybutyl groups, etc.

According to one alternative, the present invention concerns a carboxyalkyl chitosan where the alkyl part of the carboxyalkyl is linear or branched C1-C5.

According to one alternative, the present invention relates to a carboxymethyl chitosan.

According to this alternative, the substituted chitosan is an N-carboxyalkylated chitosan.

According to this alternative, the substituted chitosan is an O-carboxyalkylated chitosan.

According to this alternative, the substituted chitosan is an N-carboxyalkylated and O-carboxyalkylated chitosan.

This invention, according to a second aspect, relates to a chitosan derivative with glucosamine units, N-acetyl-glucosamine units and glucosamine units substituted with a carboxyalkyl group, said carboxyalkyl chitosan having a zeta potential, measured at pH 7.5, lower than or equal to −10 mV, and preferably lower than or equal to −15 mV. More particularly, such a chitosan derivative allows limiting the immune response of a subject to whom the chitosan derivative or a composition having it has been administrated, typically by instillation, injection or implantation.

Advantageously, the zeta potential, measured at pH 7.5, is lower than or equal to −18 mV.

Advantageously, carboxyalkyl chitosan has a zeta potential, measured at pH 7.5, lower than or equal to −22 mV, and preferably lower than or equal to −24 mV.

According to one specific alternative, the substituted chitosan has a degree of substitution (DS) from 20 to 80%, and preferably from 40 to 60%, and a degree of acetylation (DA) from 30 to 80%, and preferably from 30 to 75%.

According to one specific alternative, the substituted chitosan has a degree of substitution from 50 to 200%, and preferably from 70 to 200%, and a degree of acetylation from 30 to 80%, and preferably from 30 to 75%.

According to another specific alternative, the substituted chitosan has a degree of substitution from 90 to 200%, and preferably from 90 to 150%, and a degree of acetylation from 30 to 80%.

According to one specific alternative, the substituted chitosan has a degree of substitution from 90 to 200%, and preferably from 90 to 150%, and a degree of acetylation from 30 to 60%.

According to one specific alternative, the substituted chitosan has a degree of substitution from 90 to 200%, and preferably from 90 to 150%, and a degree of acetylation from 40 to 75%.

By substituting the chitosan, it has been possible to prepare a solution of one carboxyalkyl chitosan soluble in an aqueous solution with a pH varying over a broad range, whereas non-substituted chitosan is soluble only at a pH lower than a pH of about 6. Carboxyalkyl chitosan indeed has a capacity to be solubilised at different pH by virtue of the presence of carboxyalkyl groups which modify its solubility profile, and more particularly the physiological pH or other pHs when the physiological fluids are modified by a pathology, for example an inflammatory pathology.

By «water soluble» it is meant that the carboxyalkyl chitosan exhibits no cloudiness visible to the naked eye when put in an aqueous solution. More specifically, solubility, that is the lack of cloudiness, of a solution of carboxyalkyl chitosan at a concentration of 1% (m/m) for example in water or a buffer solution, for example a phosphate buffer, can be confirmed by an optical density lower than 0.5, and preferably lower than 0.2, measured by UV-visible spectrometry at the wavelength of 500 nm in reference to a reference tank including only the aqueous solvent used for the sample measured, but in the absence of the substituted chitosan. Another method consists of a visual inspection according to the monography 2.9.20 of the European Pharmacopeia. When the chitosan is not sufficiently substituted, the composition is not soluble in a satisfactory pH range, for example from pH 5.5 to pH 8.5, at room temperature.

According to one alternative, the carboxyalkyl chitosan is sterile.

By «crosslinked by covalent bonds between the carboxyalkyl chitosan chains» it is meant that the main chitosan chain (also called chitosan backbone) is covalently bonded with one or more main chitosan chains. A three-dimension network of chitosan molecules is thus advantageously obtained. The invention is not limited to a specific covalent crosslinking method, but the preferred method uses a chemical molecule used as crosslinking agent, also called a crosslinking agent. The notion of «crosslinked by covalent bonding between the carboxyalkyl chitosan chains» more particularly concerns covalent bonds involving crosslinking agents bonding carboxyalkyl chitosan molecules. These are however covalent bonds between carboxyalkyl chitosan chains by means of atom chains (typically the part of the crosslinking agent located between its reactive functions).

According to the invention, the carboxyalkyl chitosan is crosslinked.

Beads

Advantageously, according to the invention, the beads include or are made of a hydrated matrix in the form of a hydrogel.

By hydrogel, it is intended the conventional meaning of this word, and especially a three-dimensional (3D) network of at least one hydrophilic polymer which can swell in water and retain a significant amount of water while preserving its structure due to the crosslinking of the individual chains of the polymer(s). A hydrogel bead is a hydrated bead containing at least 70% water by mass with respect to its total humid mass. Typically, a hydrogel bead is able to retain this water mass in ambient conditions or after administration in a tissue.

According to one alternative, the matrix comprises at least one polymer, for example at least one hyaluronan, possibly crosslinking on itself by covalent bonds and/or crosslinked by covalent bonds with carboxyalkyl chitosan.

By «crosslinked on itself» or «on themselves», it is meant that the molecules can include covalent bonds of intra- and/or inter-chain molecular crosslinking.

Advantageously, the matrix according to the hydrogel invention comprises or is made of one or more bioresorbable polymers including at least one carboxyalkyl chitosan.

According to one alternative, the matrix according to the invention forming a hydrogel is made of a carboxyalkyl chitosan.

According to one alternative, the matrix according to the invention forming a hydrogel includes or is made of a carboxyalkyl chitosan crosslinked on itself and/or co-crosslinked with another polymer, and one or more other biopolymers, possibly crosslinked or co-crosslinked with the carboxyalkyl chitosan.

Thus the invention includes several alternatives, including:

An alternative in which the hydrogel matrix comprises or is made of a carboxyalkyl chitosan crosslinked on itself and without any other polymer in the hydrogel matrix.

An alternative in which the hydrogel matrix comprises or is made of a carboxyalkyl chitosan crosslinked on itself and one or more polymers, crosslinked on themselves or not, in the hydrogel matrix.

An alternative in which the hydrogel matrix comprises or is made of one carboxyalkyl chitosan co-crosslinked with one or more other polymers, and in which the carboxyalkyl chitosan and/or the other polymers may be crosslinked on themselves.

Thus, according to one alternative, said carboxyalkyl chitosan is co-crosslinked with another polymer.

According to one alternative, the bioresorbable polymers according to the invention are natural biopolymers and for example naturally occurring in human or animal tissue, for example they may be polysaccharides, proteins and any other polymer present at the tissue, cell level. According to one embodiment the biopolymer other than carboxyalkyl chitosan is chosen from polysaccharides or proteins, and preferably chosen along the following biopolymers or any of their combinations: elastin, hyaluronan, chondroitin, fibrin, collagen, dextran, cellulose, carboxyalkyl cellulose, lubricin, mucin, silk, albumin, and any derivative thereof.

A biopolymer may be native to have a modified native structure.

According to one alternative, the other biopolymer is chosen from a polysaccharide, oxidised or not, crosslinked by covalent or non-covalent bonds, for example a glycosaminoglycan, and more particularly a hyaluronan, as for example hyaluronic acid, sodium hyaluronate or any salts or derivatives thereof.

According to one alternative, the bioresorbable polymers are synthetic polymers.

According to one alternative, the matrix according to the invention making up the hydrogel beads comprises or is made of a carboxyalkyl chitosan and a hyaluronan, the carboxyalkyl chitosan being crosslinked on itself and/or co-crosslinked with the hyaluronan. These two polymers are advantageously crosslinked on themselves and/or co-crosslinked together.

One of the preferred objects of the invention is to associate these two polymers to be able to adapt the intended properties of the beads, for example to modulate the water content of the beads, their biomechanical properties and/or the bioresorbability kinetics.

According to one alternative, the hyaluronan used for preparing the beads has an average molecular mass lower than 5,000,000 as determined by capillary viscometry or steric exclusion chromatography. The molecular mass of the hyaluronan is sometimes expressed via its intrinsic viscosity by capillary viscometry, properly correlated with the molecular mass via the Mark Houwink relationship. Thus, the hyaluronan used for the preparation of the beads may exhibit an intrinsic viscosity which is «high» according to one alternative (from about 3 to 4.25 $m^3/kg$), «medium» (from 1.5 to 3 $m^3/kg$) according to another alternative, or «low» (from 0.1 to 1.5 $m^3/kg$) according to another alternative, depending on the intended properties for the beads.

According to one alternative, the hyaluronan is obtained by fermentation, for example with *Streptococcus equii*. According to another alternative, it is produced by initial extraction from cock's combs.

According to one alternative, the matrix includes at least one hyaluronan crosslinked by covalent bonds.

Thus, the crosslinked hyaluronan comprises covalent bonds between different hyaluronan chains.

Different types of hyaluronan can be crosslinked together, such as hyaluronans with different molecular masses or different hyaluronan salts.

Thus the invention relates to a hydrogel in the form of beads comprising or made of a matrix including at least one hyaluronan co-crosslinked by covalent bonds with the carboxyalkyl chitosan.

Preferably, the beads according to the invention have a water content higher than 80%, preferably higher than or equal to 85%, for example higher than 90%, in mass with respect to the total mass of the bead.

Advantageously, the beads according to the invention are not toxic in humans or animals; that is without toxic component or degrading into a toxic component, such as checked according to the standards applicable for the product and the targeted indication, according to whether it is a medical device, a drug or a veterinary product, for example using an in vitro cytotoxicity model and/or an animal model, for example to check the lack of chronical toxicity after oral or systemic administration.

Advantageously, the beads are biocompatible and have no local tolerance issue, or immunoreactivity unacceptable for the targeted indication, for the tissue in or on which they are administrated.

According to one advantageous alternative, the beads according to the invention do not include any compound of animal origin.

According to one advantageous alternative, the beads according to the invention do not include any alginate, gelatine, carrageenan or native chitosan, that is which is not a chitosan derivative.

According to one advantageous alternative, the beads according to the invention include at least one carboxyalkyl chitosan and possibly a hyaluronan. The hyaluronan designation includes hyaluronic acid and its salts.

Advantageously, the beads according to the invention are bioresorbable, preferably with a long residence time or adaptable to the targeted indication. By «bioresorbable», it is meant a polymer which is degraded/absorbed gradually by natural biological/physiological phenomena, and typically over several days, preferably over several weeks or months (maximum time according to the targeted indication), into compounds of low molecular mass, which can be removed when it is injected by subcutaneous or intradermal route, in the body of a warm-blooded animal or a human being.

Advantageously, the beads according to the invention are sterilisable, preferably by wet heat sterilisation. Advantageously, the beads according to the invention maintain essentially their characteristics and properties after sterilisation, particularly in wet heat or by filtration. The beads are preferably sterilised once in suspension during a final phase.

Advantageously, the beads according to the invention are injectable through a needle adapted to the indication, that is the force applied to inject them should be acceptable, that the injection action should not cause jerking, and that it must not cause any alteration to the ejected beads. The injection force guarantees a simple, precise and well-controlled medical act. The injection must occur regularly and smoothly; thus an «easy injection of the beads or compositions is preferred according to the invention. An «easy injection indicates preferably that the force to apply to a syringe is lower than 50 Newton, preferably lower than 40 Newton, to flow a composition according to the invention through a needle defined for the targeted application and with an appropriate piston ejection speed (for example at a speed of 10 mm/min). For example, for applications in dermatology, beads injectable through a needle in a diameter range from 25G to 34G are preferred. For example, for applications in ophthalmology, beads easily injectable through a needle in a range from 27G to 34G are preferred. For example, for applications in rheumatology, beads easily injectable through a needle in a range from 18G to 25G are preferred.

Advantageously, the beads according to the invention have the characteristics sought after injection, implantation or instillation via the administration device employed.

According to one alternative, the hydrogel beads according to the invention have an average diameter from 20 μm to 450 μm under their hydrated form. The average diameter of the beads is measured according to a particle size analysis method, for example by laser diffractometry (average volume diameter), or by analysis of images recorded by a microscopy technique (average diameter in number), for example optical, scanning electron sweep, atomic force or confocal scanning microscopy. These techniques also enable measuring the diameter of the beads under their dehydrated form.

According to one alternative, the beads according to the invention have an average volume diameter from 25 μm to 250 μm under their hydrated form, particularly to minimize the response to a foreign bodies and prevent the beads from migrating in the tissues.

According to one alternative, the hydrogel beads according to the invention have an average volume diameter between 1 μm and 20 μm under their hydrated form.

According to one alternative, the hydrogel beads according to the invention have an average volume diameter lower than 1000 nm and preferably lower than 500 nm. These are nanobeads, nanoparticles of hydrogel or nanogel.

Typically, the distribution of bead size depends on the targeted application.

The beads are spherical to minimize reactions to foreign bodies after injection or implantation and in a manner adapted to the targeted indication.

Advantageously, the beads according to the invention present a surface morphology with little roughness and preferably smooth, in their hydrated form.

Advantageously, a smooth or non-rough surface minimises reactions to foreign bodies.

Advantageously, the beads according to the invention have a negative or neutral surface charge, particularly by measuring the zeta potential. Advantageously, a negative or neutral surface charge minimises reactions to foreign bodies.

For many applications of the beads, homogenous hydrogel beads are preferred, that is not fragmented and without solid component within or on the surface of the beads.

Advantageously, the beads are transparent.

Beads of a hydrogel remaining integral and homogenous when incorporated in their final phase (medium), for example an aqueous phase, and their final packaging, for example a syringe, as well as throughout their storage time are also preferred for many applications. These are called «integral» and «homogenous» beads.

Mechanical Properties

Advantageously, the beads according to the invention are flexible under their hydrated form, that is their shape can be modified when they are subjected to some deformation force (for example compression or shearing), without breaking and are able to return to their initial shape once the bead is released from the deformation force.

Advantageously, the beads according to the invention exhibit proper resistance to mechanical stresses imposed by the implantation site.

Advantageously, thus the beads according to the invention have a proper capacity to increase, fill and/or remodel a tissue into which they are injected or implanted.

Physiological Properties

Advantageously, the beads according to the invention are suitable for use in human beings or animals, particularly in terms of safety, immunocompatibility, bioresorbability, biomechanical properties and life or activity time. Yet the compositions of the state of the art do not offer such properties satisfactorily and would be thus not in accordance with the present invention.

Preparation Process

This invention also relates to a bead preparation process according to the invention.

This invention more particularly relates to a process for preparing a plurality of beads such as defined according to the invention, said process including:

preparing an aqueous solution of a carboxyalkyl chitosan, in the presence or not of at least one other polymer, with a least one crosslinking agent, preferably made at alkaline pH;

forming droplets of this solution in the form of a plurality of beads;

crosslinking the carboxyalkyl chitosan, and possibly at least the other polymer if present, by the crosslinking agent; and obtaining a plurality of beads as defined according to the invention.

In particular, the process according to the invention comprises forming droplets based on the bioresorbable polymers, then stabilising them by covalent crosslinking of the polymers.

Typically, a process according to the invention comprises dissolving a carboxyalkyl chitosan and possibly other polymers and forming droplets of this solution, and then covalently crosslinking in the form of hydrogel beads, possibly classifying them to select the dimensions of beads desired.

According to a preferred alternative, the beads are incorporated into an aqueous phase, possibly comprising one or more other polymers.

According to one embodiment, one or more active agents are added in the aqueous solution comprising carboxyalkyl chitosan, and possibly one or more other polymers, before the formation of droplets. A solution or a suspension comprising at least one active agent, whether the active agent is soluble or insoluble in this aqueous solution, respectively, can thus be prepared and then the beads according to the invention can be formed, in order to encapsulate one or more active agents in the beads.

Dissolution

According to a preferred embodiment, a carboxyalkyl chitosan, and possibly one or more other polymers, are dissolved in an aqueous solution containing the crosslinking agent, preferably with an alkaline pH. Advantageously, the aqueous solution also includes one or more crosslinking agents.

The alkaline agent is typically soda, for example at a mass concentration between 0.1 and 5%.

According to one embodiment, in this dissolution step the carboxyalkyl chitosan can be mixed with other water soluble polymers, for example a biopolymer, for example a polysaccharide, for example hyaluronan.

Formation of Droplets

According to one embodiment, the droplets are placed in the presence of an aqueous phase possibly comprising an organic solvent, for example an alcohol, for example ethanol.

According to one embodiment, the process includes coagulating the droplets, in the presence of at least one coagulation agent, in the form of a plurality of beads before their crosslinking.

Advantageously, the process comprises forming carboxyalkyl chitosan droplets and possibly one or more other polymers if present, possibly followed with coagulating the droplets, for example by ionic gelling (non-covalent bonds).

Conventional processes can be used for forming the droplets of the solution or the polymers. The polymer droplets can be formed by emulsification in hydrolipidic, oil in water or water in oil medium.

Droplets can be formed by passing the solution through any tube in a diameter adapted to the intended bead diameter, at an appropriate flow rate.

This can also be performed using a sprayer (also called a nebulizer) with a given diameter, for example using a binary nozzle, by controlling the flow rate and/or pressure. As an illustration, to obtain beads in a diameter mostly lower than 400 μm (D0.9), a binary nozzle of a diameter of 2.8 mm (Büchi) is used. To change the diameter of the droplets, we adapt the droplet forming system, for example the internal diameter of the nozzle. According to one alternative, the droplet forming system or its parameters are adapted according to the viscosity of the polymer solution. Other processes also exist, for example laminar jet electromagnetic (for example with the VAR-D continuous equipment marketed by Nisco), or electrostatic, with coaxial air flow, with dynamic air flow, by ultrasound or by continuous extrusion by cutting the solution jet using a rotating tool (for example Jetcutter, Genialab).

According to one embodiment, a coagulation of the droplets is performed in a solution designated as «coagulation bath» comprising a coagulation agent. According to one alternative, the agent is a chloride of alkaline earth metal, typically calcium chloride, which induces gelling by ionic interactions with carboxyalkyl chitosan.

According to one embodiment, the coagulation bath is an aqueous solution in the presence of a solvent of the alcohol type, for example ethanol.

Preferably, the coagulation bath is made of a water/solvent volume ratio of 90/10 to 10/90, typically 30/70, 20/80 or 80/20.

Preferably, the concentration of calcium chloride in the coagulation bath is from 10 to 200 mg/mL.

Preferably, coagulation is achieved at room temperature, that is without heating, preferably at a temperature from 20 to 25° C.

According to one embodiment, comprises a step of classifying the coagulated beads to control their distribution.

Cross-Linking

According to one alternative, the plurality of beads obtained after crosslinking is subjected to purification steps by washing and balancing the pH and osmolality in a physiologically acceptable medium.

Advantageously, the process comprises crosslinking the polymer(s) shaped in the form of droplets, possibly coagulated, preferably via a crosslinking agent present in the polymer solution as early as the first step.

According to one alternative, the crosslinking is formed by a crosslinking agent forming said covalent bonds.

Thus several chitosan chains can be crosslinked, for example by reaction with one or more crosslinking agent(s), such as for example chosen from the crosslinking agents used for crosslinking biopolymers, particularly polysaccharides, such as for example 1,4 butanediol diglycidyl ether, 1-bromo-3,4-epoxybutane, 1-bromo-4,5-epoxypentane, 1-chloro-2,3-epithio-propane, 1-bromo-2,3-epithiopropane, 1-bromo-3,4-epithio-butane, 1-bromo-4,5-epithiopentane, 2,3-dibromopropanol, 2,4-dibromobutanol, 2,5-dibromopentanol, 2,3-dibromopro-panethiol, 2,4-dibromobutanethiol, and 2,5-dibromopentane-thiol epichlorohydrin, 2,3-dibromopropanol, 1-chloro-2,3-epithiopropane, dimethylaminopropylcarbodiimide, gallic acid, epigallocat-echine gallate, curcumin, tannic acid, genipine, or diisocya-nate compounds such as hexamethylene diisocyanate or toluene diisocyanate, or even divinyl sulfone.

Genipine is a crosslinking agent of natural origin used to cross-link polysaccharides, particularly carboxymethyl chi-tosan (Yang et al. Ophthalmic drug-loaded N,O-carboxym-ethyl chitosan hydrogels, Acta Pharmacol Sin 31, 1625, 2010). Genipine colours the hydrogel in dark blue to black, which can be of advantage in some indications.

Preferably, the crosslinking agent is an agent of the polyepoxide type, for example bifunctional. Preferably, 1,4-butanediol diglycidyl ether (BDDE) or ethylene glycol diglycidyl ether (EGDE), is used as crosslinking agent, as they are already used for the preparation of biomaterials applied to humans, particularly hyaluronan hydrogels for intradermal, intra-articular or intra-ocular administration. According to one alternative, the crosslinking agent is divinyl sulfone.

Typically, crosslinking occurs at the appropriate pH, depending on the crosslinking agent and the types of bonds considered.

According to one alternative, crosslinking is performed in alkaline aqueous phase, for example in the presence of a sodium hydroxide (NaOH) solution. Advantageously, con-centration in carboxyalkyl chitosan present initially in the aqueous phase is in the 1 to 30% range and preferably from 5 to 20% (m/v) in mass of carboxyalkyl chitosan with respect to the volume of alkaline aqueous phase.

Advantageously, the amount of crosslinking agent is 0.001 mol to 0.1 mol BDDE per gram of the polymer(s).

Preferably, the amount of crosslinking agent is from 0.005 to 0.02 moles per gram of polymers when using BDDE.

Typically, crosslinking occurs at a temperature and dura-tion to be adapted to each case, depending on the crosslink-ing agent, polymers and biomechanical properties sought.

Generally, crosslinking is followed with neutralising the medium, for example by adding an acid, and for example by adding acetic acid or hydrochloric acid.

Purification

Advantageously, the process comprises purifying the crosslinked beads. Purification allows on the one hand to significantly remove excess coagulation agent and unreacted crosslinking agent, and on the other hand to balance the hydrogel of the beads in terms of pH and osmolality with the medium selected, for example a physiologically acceptable medium, such as a buffer solution.

According to one embodiment, purification includes one or more washings with a solution comprising a buffer agent, preferably a saline phosphate buffer (often abbreviated PBS, standing for phosphate buffered saline) or the medium in which the beads are to be included according to the targeted product.

Preferably, purification includes one or more washings with pharmaceutical grade water and then with a physiologi-cal solution, that is a solution having pH and osmolality appropriate for one injection or an implantation in tissue.

Advantageously, purification is performed by a series of filtration/washing steps on a filtering membrane or by dialy-sis using the selected solution and an appropriate cut-off dialysis membrane.

According to one embodiment, the hydrogel beads are first neutralised by adding hydrochloric acid; and then collected on a filtering membrane under vacuum. This operation can be repeated several times. The beads can then be suspended in a buffer solution (of composition, osmola-lity and pH chosen according to the indication), and collected by filtration according to a conventional technique. This step is renewed until obtaining a suspension of hydro-gel beads with the osmolality and pH of the buffer desired, and a content in residue in the beads lower than the limits specified beforehand for the targeted product, in connection with the amount delivered and its indication. Thus, it is checked that the coagulation agent content and the residual content on crosslinking agent in the beads are lower than the limits specified. The content in coagulation agent is deter-mined according to the total ash method of the European Pharmacopeia in the case of calcium chloride. The content in crosslinking agent is determined by LC-MS in the case of the BDDE, based on a method as described by Fidalgo et al. (Detection of a new reaction by-product in BDE crosslinked autoclaved hyaluronic acid hydrogels by LC-MS analysis, Medical Devices: Evidence Res 11, 367, 2018).

Sorting/Classification

According to one alternative, the plurality of the beads is classified to select beads depending on their dimensions.

Optionally, smaller beads are removed, by allowing the higher size beads to settle. And then, the hydrogel beads can for example be sorted depending on their size according to conventional sorting methods (by «sieving»), placing them on a sieve with an appropriate porosity stirred by ultrasound, by vacuum filtration with decreasing porosity filters, or by any other sorting method.

Preservation

According to one embodiment, the hydrogel beads obtained are preserved by incorporating them to an aqueous solution, for example a buffered solution such as the phos-phate buffer or any other aqueous solution, until they are finally formulated, sterilised and packaged.

According to one embodiment, the hydrogel beads obtained are dehydrated, for example by freeze-drying or drying in a vacuum oven and preserved in the dry state.

According to one particular embodiment, the bead prepa-ration process according to the invention includes:

solubilising a mixture of carboxyalkyl chitosan mix, another polymer, and preferably a hyaluronan, and at least one crosslinking agent, in alkaline phase;

forming droplets of carboxyalkyl chitosan and the other polymer, and preferably a hyaluronan, and then possi-bly coagulating them in a coagulation bath comprising a coagulation agent, for example via ionic gelling;

performing crosslinking reaction on the droplets;

obtaining beads of a co-crosslinked matrix of carboxyal-kyl chitosan and the other polymer, and preferably a hyaluronan.

Thus, for example a process according to the present invention includes:

preparing a solution of carboxyalkyl chitosan (and pos-sibly another polymer, and preferably a hyaluronan) and 1,4 butanediol diglycidyl ether (BDDE) in a basic solution containing NaOH; and then the solution is dispersed in droplets in a coagulation bath comprising a coagulation agent, typically calcium chlo-ride in a water/ethanol mix, at room temperature, which causes them to be coagulated in the form of spherical beads; and then crosslinking the carboxyalkyl chitosan (and possibly the other polymer) by the BDDE to provide hydrogel beads of crosslinked carboxyalkyl chitosan;

neutralising and washing the hydrogel beads of cross-linked carboxyalkyl chitosan, in order to remove the excess coagulation agent and BDDE and balance the hydrogel of the beads at the pH and osmolality desired;

optionally, sorting the hydrogel beads depending on their
   size.

Beads in the form of hydrogel comprising a matrix according to the invention are thus obtained.

According to one alternative, a matrix according to the invention is sterile.

It is advantageous to provide a hydrogel in the form of beads from a matrix according to the invention according to this process.

Composition

Advantageously, the composition of the invention can also include a polymer other than the crosslinked carboxyalkyl chitosan, particularly in the phase associated with the beads. Thus, if the composition comprises an aqueous phase, according to one alternative, the aqueous phase and/or the beads include one or more polymers.

According to one advantageous alternative, the polymer (of the associated phase and/or the beads) is a biopolymer, for example a polysaccharide, oxidised or not, crosslinked by covalent or non-covalent bonds, for example a glycosaminoglycane, and more particularly a hyaluronan, as for example sodium hyaluronate or one of its derivatives. According to one alternative, the phase associated with the hydrogel beads also includes a carboxyalkyl chitosan, crosslinked or not.

One advantage of combining or crosslinking a carboxyalkyl chitosan with some other polymers is to add their properties, or even create synergies.

According to one alternative, the plurality of beads is associated with an aqueous phase, a lipophilic phase, a hydrolipidic phase, or another solid phase, possibly comprising one or more polymers, for example a carboxyalkyl chitosan, a hyaluronan, or any combination thereof.

According to one advantageous alternative, the aqueous phase composition and/or the beads are in the form of a hydrogel with pH and osmolality in balance with a physiological medium.

According to one alternative, the phase in which the beads are associated is specific to the injection into a human or animal body.

According to one advantageous alternative, the aqueous phase and/or the beads are in a form specific to the injection into a human or animal body.

The invention is also related to a composition administrable to humans or animals, said composition comprising a plurality of beads as defined according to the invention.

According to one preferred alternative, the hydrogel beads according to the invention are formulated in the form of dispersion or suspension in an injectable aqueous medium (possibly slightly viscous) in humans or animals. This is generally referred to as a composition according to the invention.

According to one alternative, the composition is formulated as an injectable suspension, ready for instillation or implantable in humans or animals.

According to one advantageous alternative, particularly for products intended for cutaneous injection, the beads sorted or not are incorporated in a solution of one or more hydrophilic biopolymers, preferably a hyaluronan.

According to one alternative, the formulation of beads is conditioned in a device adapted to delivery, for example a syringe, and then an appropriate sterilisation is performed, for example by autoclave, by applying a cycle intended to ensure sterility. According to one alternative, the invention thus relates to sterile syringes containing formulations of hydrogel beads based on crosslinked carboxyalkyl chitosan, ready for delivery by injection.

The mass ratio [carboxyalkyl chitosan/hyaluronan] is for example from 5/95 to 95/5, for example from 10/90 to 90/10, for example from 20/80 to 80/20 and again for example from 30/70 to 70/30. According to one alternative, the mass ratio [carboxyalkyl chitosan/hyaluronan] is 1/1 (that is 50% chitosan and 50% hyaluronan).

The aqueous medium can be water, an aqueous solution, with a pH and the osmolality are for example adjusted using a buffer solution with addition of salts and/or possibly polyols, for example sorbitol, mannitol, glycerol and/or trehalose.

According to one embodiment, the composition of the matrix has an osmolality from 100 to 700 mosm/kg, preferably from 120 to 500 mosm/kg.

According to one embodiment, the composition of the matrix has an osmolality from 100 to 500 mosm/kg, preferably from 120 to 270 mosm/kg.

Advantageously, osmolality of the composition of the matrix is included between 250 and 400 mosm/kg, and preferably 280 to 350 mOsm/kg.

According to one alternative, the composition of the matrix has an osmolality appropriate to an articulation.

According to one alternative, the composition of the matrix has an osmolality compatible with an ocular or intraocular surface.

According to one alternative, the composition of the matrix has an osmolality compatible with the dermis and hypodermis.

According to one alternative, it is preferable for the osmolality of the composition of the matrix ranges between 100 and 400, and more specifically between 120 and 350 mosm/kg.

According to one alternative, a composition according to the invention is sterile.

Advantageously, the composition according to the invention is contained in an injection, implantation, or instillation device, as for example a syringe or a vial. Advantageously, the injection device, as for example a syringe, can then undergo a steam sterilisation. This device, for example a syringe, can then be packaged, preferably in an aseptic or sterile manner. This can also be a pouch, a capsule, or a vial allowing instillation of the composition according to the invention filled in an aseptic way after sterilisation of the formulation, or sterilised directly after filling.

According to one alternative, a composition according to the invention, and more particularly comprising hydrogel beads according to the invention, is sterilised by filtration and/or steam sterilisation, before filling an injection, implantation or instillation device, as for example a syringe or a vial.

The skilled person knows sterilisation techniques of a hydrogel to obtain a sterile hydrogel desired. He/she has available several types of equipment to sterilize by heat or steam, and can use several types of cycles which removes the microbial charge.

This invention more particularly relates to an injectable composition comprising hydrogel beads according to the invention.

The invention also relates to a pharmaceutical composition comprising at least hydrogel beads according to the invention.

According to one alternative, the composition according to the invention is used as a pharmaceutical composition injectable, implantable or ready for instillation, or a medical device injectable or implantable or ready for instillation.

The invention also covers a composition according to the invention under a dry form, particularly in a freeze-dried form. The freeze-dried product can be more particularly (re)dispersed prior to use.

This invention more particularly relates to a composition according to the invention for a use for a therapeutic treatment, for example comprising the injection by subcutaneous, intradermal, intraocular, or intra-articular, intra-mucosae, intra-peritoneal, intra-muscular injection of said composition, for example for repairing, regenerating or filling at least one bodily tissue/liquid requiring repairs or filling.

It is advantageous to use a chitosan with sufficient degree purity for the application considered.

It is advantageous to use a hyaluronan with sufficient degree purity for the application considered.

The biomechanical properties sought by the composition according to the invention can vary in nature and in amplitude according to the indication, for example according to the tissue in which the hydrogel must be integrated, the action mechanism or the effect intended to offer benefits for the patient and the duration of the effect.

Advantageously, the properties of the composition according to the invention, and more particularly hydrogel beads according to the invention, are adapted to the indication. To adapt these properties, the end concentration in polymers (carboxyalkyl chitosan and/or other polymers such as a hyaluronan), and/or the crosslinking rate is adjusted for example, particularly via the crosslinking agent/polymers mass ratio, and/or the nature and/or the amount of ions, and/or the initial molecular mass of the polymer(s) and/or the process for preparing polymer droplets.

Particularly, the invention relates hydrogel beads according to the invention which are elastic, particularly when a durable volume increase is required on the cutaneous, hypo-dermic (subcutaneous) or periosteal level. The invention is related more particularly beads in suspension in a continu-ous phase. This phase can also offer a variable viscoelastic-ity or other advantageous properties for the target product, for example a lubricating effect. More particularly for a product with intra-articular use, this allows both impacts to be absorbed and cartilage to benefit from a lubricating effect. A composition of the invention can have a variable level of elasticity, adjusted according to the indication, and which can be characterised by the measurement of the elastic modulus by rheometry.

This invention also relates to the compositions compris-ing a phase including a plurality of hydrogel beads accord-ing to the invention. It can be said that the beads are incorporated in this phase.

According to one alternative, the phase comprising the beads is an aqueous phase.

According to one alternative, the phase comprising the beads is a lipophilic phase.

According to one alternative, the phase comprising the beads is a hydrolipidic phase, and more particularly an emulsion, as for example direct, reverse, single, multiple, etc.

According to one alternative, the phase comprising the beads is a solid phase.

According to one specific alternative, the phase compris-ing the beads is a continuous aqueous phase.

This invention relates to an injectable composition char-acterised in that it includes hydrogel beads according to the invention and one phase in which the beads are incorporated.

This invention relates to a pharmaceutical composition comprising hydrogel beads according to the invention.

According to one alternative, the composition is formu-lated as a pharmaceutical composition or composition for the implementation in a therapeutic treatment method.

According to one alternative, the composition is used as a pharmaceutical composition injectable, implantable or ready for instillation, or topical delivery, or medical device injectable or implantable or ready for instillation, or topical delivery, for example for a use in a therapeutic treatment method, for example comprising the instillation or topical delivery or injection by subcutaneous, intradermal, mucosal, ocular, intraocular, or intra-articular route, of said compo-sition, for example for repairing or filling at least one body tissue requiring repairing or filling.

According to one alternative, the composition according to the invention is used in a method for the treatment, repairing or filling of at least one body liquid or tissue requiring a repair or filling, and for example the bodily tissue of which is chosen from the tissues belonging to vocal chords, muscles, ligaments, tendons, mucous, sexual organs, bones, joints, eyes, dermis, or any one of the combinations, and more particularly the dermis, cartilage, synovial mem-brane, a cutaneous wound or the ocular surface.

This invention relates to a composition according to the invention for use in a treatment method of arthrosis, or the repair of a lack of cartilage, for example by injection into a biological fluid, for example the synovial fluid, or after mixing with a biological fluid, for example the blood and implantation in the cartilage. A biological fluid is a fluid of bodily origin having or not undergone a treatment modifying its composition.

This invention relates to a medical device, for example a medical implant, characterised in that it comprises or con-sists in a composition as defined according to the invention.

This invention relates more particularly according to the invention for use in a treatment in therapeutic, surgery or cosmetics, including more particularly a treatment in rheu-matology, ophthalmology, gynaecology, cosmetic medicine, plastic surgery, internal surgery, orthopaedic surgery, gynaecological surgery, for the prevention of post-surgery tissue adherence, in dermatology.

This invention also relates to a composition according to the invention for ophthalmic use, for example in therapeutic treatment of a dry eye syndrome, a cornea lesion, or for intraocular delivery in any other ocular tissue.

This invention also relates to a composition according to the invention by instillation on the ocular surface to prevent or treat a cornea lesion, or dry eye syndrome, more particu-larly in order to lubricate or regenerate the ocular surface.

Indeed, the invention also concerns a composition of ophthalmic drops comprising a carboxyalkyl chitosan defined according to the present invention.

According to one alternative, the subject is impacted by an inflammatory pathology of the joints (for example osteoarthrosis, arthritis, etc.).

This invention is related more particularly to a composi-tion according to the invention for the treatment of an arthrosis, arthritis, or repairing of a lack of cartilage, for example by injection in the synovial cavity or by implan-tation on the level of the lack of cartilage.

This invention is related more particularly to a medical device, for example a medical implant, characterised in that it comprises or consists in a composition according to the invention.

According to one preferred alternative, the invention thus relates to a medical device comprising a chamber containing a composition according to the invention in a dry form, particularly under a freeze-dried form, and possibly one or more other chambers containing one or more active, additive or excipient products.

The composition according to the present invention can also include one or more active agents for a desired indication, and/or one or more additives or excipients allowing to modulate the properties of the composition according to the invention.

According to one alternative, the beads according to the invention comprise, or in other terms encapsulate, one or more active agents for a desired indication, and/or one or more additives or excipients allowing to modulate the properties of the composition according to the invention. For example they can be pharmaceutical active ingredients or nutrients for the zone of delivery and more particularly for the injection, instillation or implantation zone.

This invention also relates to a composition according to the invention formulated as pharmaceutical composition or composition for the implementation in a therapeutic treatment method.

This invention also concerns a composition according to the invention for the preparation of a pharmaceutical composition or a medical device.

This invention also relates to a composition according to the invention for use in a treatment method of arthrosis, or the repair of a lack of cartilage, for example by injection in the synovial pocket or after mixing with a biological fluid, for example the blood and implantation in the cartilage/bone.

This invention also relates to a composition according to the invention for a use in a method of treatment or cosmetic care by filling cutaneous tissue. More particularly for example this means injecting a composition according to the invention in subcutaneous, intradermal, intra-mucosal, intramuscular.

This invention also relates to a composition according to the invention for a use in a method of treatment of the skin by multiple injection by intradermal route or other tissues. Such compositions can be used typically in dermatology, as treatment for cosmetic purpose.

This invention also relates to a composition according to the invention for a use in a method of treatment in which the composition of a viscosupplementation agent. This means for example to inject on the intra-articular level the composition of the invention particularly to limit friction of the cartilage surfaces of the joint.

This invention also concerns a composition according to the invention for a use as cellular vector, of one or more cellular types, and/or vector of one or more active agents. These must be agents active in pharmaceutical or biological terms. The composition of the invention can indeed be compatible with the presence of cells, preferably living cells. Among the living cells of interest, mention can be made of for example: chondrocytes (joint cartilage), fibrochondrocytes (meniscus), ligament fibroblasts (ligament), skin fibroblasts (skin), tenocytes (tendons), myofibroblasts (muscle), mesenchymal stem cells, red blood cells (blood) and keratinocytes (skin). The composition of the invention can also be used as a therapeutic vector for targeted, local delivery and/or controlled release of at least one therapeutic agent.

According to one alternative, the beads according to the invention comprise one or more active agents, for example a water soluble molecule (totally or partially) and/or a non-water soluble molecule. According to one alternative, the beads according to the invention comprise one or more anti-inflammatory molecules, for example a corticosteroid, particularly a glucocorticoid. An example among others of a water soluble module is ascorbic acid. Another example of water soluble active agent is dexamethasone, an anti-inflammatory agent. Another example of non-water soluble active agent is triamcinolone, also an anti-inflammatory agent. According to one alternative, the active agent encapsulated in the beads is a water soluble biomolecule of high molecular mass (for example higher than 10 kDa) and for example a protein.

The mechanism and release of the active agent will depend on its solubility profile, either by diffusion if water soluble, or by degradation of the beads, for example hydrolytic or mechanical degradation.

Advantageously, the composition and beads according to the present invention, provide a system with local and controlled release of one or more active agents. Advantageously, the composition in bead polymer according to the invention can be adapted to the target release profile, (which depends on the indication and the molecule), and thus allowing actual versatility to adapt to the encapsulation and release of different active agents.

According to one alternative, blood, or plasma, or a platelet lysate, or plasma rich in platelets, or any other biological fluid is added with the composition of the invention allowing for example to increase performance of the product.

According to one alternative, the composition according to the invention is formulated under a solid form, for example a film, a tube or a porous foam, which can release the beads once delivered.

According to one alternative, the composition is formulated under a form of a spray.

This invention also relates to a composition according to the invention for a use in a method of cosmetic treatment or care of one or more tissues or organs affected by an excessive temperature, as in the case of a burn.

This invention also relates to a composition according to the invention for use in a method of treatment of cartilage repair (for example by implantation on a cartilage defect in order to support its regeneration).

The invention relates to a physiologically acceptable composition, delivered in a topic way, by injection, instillation or implantation, intended to enter in contact with one or more living tissues subject to oxidizing stress, for example:

intra-articular injection for the treatment of osteoarthrosis (via supplementation of the synovial fluid, cartilage lubrication, absorption of shocks on the articular level, regeneration of the synovial membrane); intra-articular implantation to enhance repair of cartilage defects;

intrabone implantation to enhance osseous repair (osteoinduction/osteoconduction);

hypodermal, subcutaneous and/or periosteal injection for filling or regenerating the skin or hair follicles, to increase the volumes in case of lipoatrophy, or for the delivery of active ingredients;

ocular instillation to relieve the symptoms of the ocular surface or prevent alterations, for example for the treatment of dry eyes and cornea lesions and the delivery of active ingredients;

intra-ocular injection, for example for optimizing effectiveness of glaucoma surgery or vitreous body supplementation, as an adjuvant to ophthalmic surgery, for the regeneration of anterior or posterior ocular tissues, and/or intraocular delivery of active ingredients;

administration on internal tissues and organs to prevent post-surgery adherence;

administration on wounds, crevices, tears, cavities . . . of
tissue and organs such as skin, bone, cartilage, cornea,
tendons, meniscus, etc. in order to enhance their repair
or regeneration;

injection on the level of vulval mucus for the treatment of
vulvodynia.

for cell cultivation, as support or scaffold for the cells,
particularly in a bioreactor, for example for tissue
engineering or reconstruction or the production of
substances of interest by the cells.

This invention also relates to a composition according to
the invention forming an intra-articular viscosupplement.

Generally, the ranges of values of osmolality and pH of
the composition are adapted and usually close to the osmo-
lality and pH values of tissues in contact with the compo-
sition according to the invention.

Advantageously, the composition according to the present
invention is sterile. Very advantageously, the composition
according to the present invention is sterilised with wet heat.

According to one alternative, the compositions of the
invention are transparent or translucent.

More particularly, the invention relates to items or pack-
aging, preferably sterile, comprising one or more instillation
or injection devices pre-filled with a composition according
to the invention, more particularly in the form of hydrogel).
These devices typically enable the product to be instilled in
the form of drops or pre-filled syringes.

Advantageously, one composition of the invention can be
stored, preferably in an item or packaging appropriate for its
indication, and preferably for several months.

The composition and the beads according to the invention
can advantageously be sterilised. Thus, the invention relates
to a sterilised crosslinked carboxyalkyl chitosan. The cross-
linked carboxyalkyl chitosan is thus sterile, particularly for
those applications requiring it to be.

According to one alternative, the beads or the composi-
tion of the invention are sterilised with steam, based on a
method known to the skilled person and/or recommended by
the European Pharmacopeia.

According to another alternative, the composition can be
sterilised by filtration using appropriate filters, for example
filters with a porosity lower than or equal to 0.2 µm.

This invention also covers a method of therapeutic treat-
ment comprising injecting a composition according to the
invention.

This invention also covers the use of a composition
according to the invention for the preparation of a pharma-
ceutical composition, more particularly for a therapeutic
treatment, for example as defined more specifically by the
invention.

This invention also covers a method of cosmetic care, in
other words non-therapeutic, comprising injecting a com-
position according to the invention. For example, this can be
the treatment of lipoatrophy or filling or one or more areas
of visible damaged tissue, for example following an accident
or a surgical procedure, for cosmetic purposes.

A tissue is a set of similar cells of identical origin, grouped
into a functional set, that is participating in a same function.
The following can be cited among the tissues: dermal tissue
(for example epithelial tissue), conjunctive tissue, muscular
tissue, adipose tissue, and nerve tissue.

By «composition according to the invention» or equiva-
lent terms, it is meant a composition defined in that in the
present invention, including according to any one of its
alternatives, particular or specific embodiments, indepen-
dently or according to any combination thereof, including
according to the preferred characteristics.

Other purposes, characteristics and advantages of the
invention will appear clearly to the skilled person upon
reading the explanatory description which refers to
examples given only for illustration purposes and which
should in no way limit the scope of the invention.

The examples are fully part of the present invention and
any characteristic appearing to be new with respect to the
state of any prior art from the description taken as a whole,
including the examples, is fully part of the invention in its
functions and its generality.

Thus, each example has a general scope.

On the other hand and unless otherwise stated, in the
examples, all percentages are provided in mass and the
temperature is expressed in degrees Celsius unless otherwise
specified, and pressure is the atmospheric pressure, unless
otherwise specified.

EXAMPLE

Ejection Force Via a Thin Needle and Integrity of the Beads
after Ejection

The measurements are made using a compression bench
(Inston 5566, Mecmesin) fitted with a load cell (Instron
500N, Mecmesin) and a sample holder adapted to syringes.
A syringe in BD glass of 1 mL containing the formulation to
be tested is set to room temperature. A 27G needle (length
½", TSK) is connected to the syringe and the syringe is
placed in the sample holder. The compression cell is lowered
at a speed of 10 mm/min for a duration of 1 minute and the
homogenous gel/phase mix is collected in a watch glass. The
ejection force is determined as being the average value of the
plateau of the force curve-displacement at constant speed.
Integrity of the beads is then checked after ejection by
optical microscopy (shape, surface).

Optical Microscopy (Size, Sphericity and Visual Inspection)

Images of the beads are recorded using the Olympus
CKX-41 microscope fitted with an Olympus SC-50 camera
and the Olympus Stream image capture software, then
processed using the CellSens Dimension Desktop software.
To do this, one or two drops of a suspension of beads are
placed on a borosilicate glass slide and covered with an
object cover. The slide is then placed immediately on the
microscope plate.

To determine the dimensions and sphericity of the beads,
a 4× magnification is chosen to view 20 beads per image
minimum. Ten images are saved, then analysed with the
CellSens software to determine the dimensions of the beads
(width, length, diameter).

Sphericity of a bead equals the square quotient of its width
over its length. The final value reported is the average of
measures for each sample after analysis of 10 images
(minimum 200 beads in total). A perfectly spherical bead has
a sphericity equal to 1.

In order to perform a visual inspection aiming at checking
the lack of undesirable insoluble species at the heart or on
the surface of the beads, one to two drops of bead suspension
are placed on two slides and the beads are observed at the
4×, 10× and 40× magnifications.

Water Content

An amount of about 500 mg hydrated beads is placed on
a paper to remove any excess of non-linked water. The beads
are laid on the plate of a Moisture Analyzer MA37 (Sarto-
rius) moisture scale and dried, according to the method of
European Pharmacopeia 2.2.32. The water content is calcu-
lated by difference between the humid mass and dry mass.

Ash Content

The ash content reflects the capacity to remove the excess mineral substances during the washing steps, mainly calcium chloride during the coagulation step. The measurement is made by calcination at 600° C., according to the European Pharmacopeia method 2.4.16 (Total ash), on the beads dehydrated beforehand in an incubator under vacuum and after having measured its water content. The ash content is relative to the dry bead mass.

Content in BDDE and by-Product of Residual BDDE

The unreacted BDDE crosslinking agent is likely to be found under the native form or else in the form of a by-product. Concentration in BDDE or its residual by-product are determined by LC-MS according to a method adapted to that of Fidalgo et al. (Detection of a new reaction by-production BDDE crosslinked autoclaved hyaluronic acid hydrogels by LC-MS analysis, Medical Devices: Evidence Res 11, 367, 2018). Fr a product based on CC hydrogel beads intended for cutaneous injection, a maximum limit is imposed of 2 ppm BDDE and its by-product (total content) (De Boulle et al. A review of the metabolism of 1,4-butanediol diglycidyl ether-crosslinked hyaluronic acid dermal fillers, Dermatol Surg 39, 1758, 2013).

Bead Size (Diameter) Determination by Laser Diffractometry

The laser diffractometry measures are made using a Mastersizer 2000 (Malvern) fitted with a «hydro-unit» (Hydro 2000SM). A volume of the suspension of beads to be tested is introduced in the hydro-unit containing pharmaceutical grade water using a pipette, until a darkening level between 3% and 10% is obtained, a darkening titration was performed beforehand to determine the optimum darkening level. The hydro unit is stirred at a speed guaranteeing homogenous dispersion of the sample and the lack of bubble sin the system. The optical parameters (refraction index) used are 1.52 for the sample (bead suspension) and 1.33 for water. Each measurement is made in triplicate. The bead size distribution (in diameter) is calculated and supplied by the equipment (average of the 3 measurements). The equipment calculates the bead size distribution and the software is set to obtain the following data: mean volume diameter, diameter at 10% (D0.1), 50% (D0.5) and 90% (D0.9) of the distribution in volume.

Biomechanical Properties (Elastic Modulus) by Rheometry

The biomechanical profile of the bead suspensions in their continuous phase is characterised using a DHR-2 Hydrid Rheometer (TA Instrument) fitted with a plane geometry of 20 mm spaced by 700 μm with a Peltier, at a temperature of 37° C., a frequency of 0.7 Hz and a deformation amplitude of 0.1 at 1000%. The equipment supplies the values of the elastic modulus (G'). As each measurement is made in triplicate, the average value of G' is calculated over the 3 measurements.

Bead Surface Roughness by Confocal Laser Scanning Microscopy

A support has been designed specifically to be able to lock the suspension of the beads during the analysis by confocal laser scanning microscopy. It is a disc based on a biomaterial of the hydrated polyacrylate type (as described in patent WO 2006063994), comprising a well the beads are laid in. The beads are analysed in a suspension of saline phosphate buffer. One to two drops of the bead suspension are placed, and then the measures are made using a VK-X (Keyence) confocal laser scanning microscope, at a magnification of 20. To qualify relative roughness of the beads, the images of the beads are compared with an image of the surface of a 'mirror polished' polyacrylate slide taken as «very smooth» control and with an image of freeze-dried beads as «very rough» control.

Qualitative Evaluation of Compression Strength of the Beads 3 beads are laid flat and in triangle, they are covered with a glass slide, on which a weight with a mass increasing up to 10 g then 50 g is placed. If the beads resist to the 10 g mass, the mechanical compression strength is deemed as being «good»; and if they resist to 50 g, «very good». Lower than 10 g, the strength is considered as being not acceptable.

Carboxyalkyl Chitosan Preparation Method (in Accordance with the International Application Filed Under Number PCT/EP2020/064159)

For carboxymethyl chitosan (CC) references CC1, CC2 and CC3 of the examples, the carboxymethylation reaction of the chitosan is conducted according to the following method. A mass of 30 g chitosan of *Agaricus bisporus* origin is dispersed into 600 mL isopropanol, 41 mL water and 163 mL sodium hydroxide at 50% (m/v). A mass of 135 g monochloroacetic acid (MCA) is solubilised in isopropanol, and the solution is added to the chitosan suspension. After reaction, the polymer is recovered by precipitation in ethanol, then purified by solubilisation cycles in water and precipitation in ethanol. CC is collected after drying.

For CCs of CC1 and CC2 references, one step is added according to the following method. A 21 g mass of CC of step 1 is dispersed in 570 mL water and the pH of the solution is adjusted to a pH of about 8. A volume of 10 mL acetic anhydride is added and the solution is stirred at room temperature. The pH of the solution is adjusted and then a volume of 10 mL acid anhydride is added. The pH is adjusted to about 7.0-7.5. The CC is collected after drying.

For examples 1 to 5, the polymers used are those from Tables 1 and 2.

TABLE 1

| Characteristics of carboxymethyl chitosans (CC) [a] | | | |
|---|---|---|---|
| Reference | CC1 | CC2 | CC3 |
| Molecular mass by capillary viscometry | | | |
| Mv of the initial chitosan (k) | 230k | 222k | 225k |
| Intrinsic viscosity of the CC | 1086 mL/g | 1029 mL/g | ND |
| Estimated Mv of the CC (k) [b] | 315k | 293k | ND |
| Molecular structure by Solid phase carbon-13 NMR | | | |
| DA (degree of acetylation) mol % | ND | 56% | 27% [c] |
| DS (degree of substitution) mol % | ND | 82% | 87% [d] |

[a] origin: fungus (*Agaricus bisporus*); manufacturer: KiOmed Pharma;
[b] average molecular mass of the CC estimated from intrinsic viscosity, via the formula of Mark-Houwink log Mv = (log visco − log K)/alpha, with K = 0.0686 and alpha = 0.7638 (constants determined for native chitosan);
[c] DA value estimated from the DA of the original chitosan (measured by potentiometric titration);
[d] DS value estimated from the DS of carboxymethyl chitosan obtained by acetylation of CC3.

TABLE 2

| Characteristics of hyaluronans (HA) [a] | | | |
|---|---|---|---|
| Reference | HA1 | HA2 | HA3 |
| Supplier | Contipro | HTL-Javenech | HTL-Javenech |
| Intrinsic viscosity [c] | 2.49 m³/kg | 3.07 m³/kg | 3.00 m³/kg |
| Average molecular mass (k) | 1840k [b] | 3300k [c] | 3200k [c] |

[a] values given by the supplier;
[b] according to the steric exclusion chromatography method with MALLS detection of the supplier;
[c] according to the method by capillary viscometry of the supplier.

Example 1—Preparation of Beads Formed by Ionic Gelling and then Covalent Crosslinking with the BDDE In this example, it is attempted to form CC beads using a process consisting in first coagulating polymer drops by calcium chloride, by ionic gelling, and then stabilizing them by covalent crosslinking by adding a crosslinking agent, 1,4 butanediol diglycidyl ether (BDDE, Alfa Aesar, CAS [2425-79-8]). The success of the process is determined by evaluating the ability of the beads to withstand the aqueous medium washing steps and then, when they withstand washing, their ability to withstand slight manual compression.

3 solutions CC reference CC2 (Table 1) are prepared in water, at a concentration of 40 mg/mL. The pH of the solutions is adjusted to 3, 6 or 13 by adding either hydrochloride acid 1N and/or sodium hydroxide 1N up to the desired pH, they are diluted at 30 mg/mL by adding water and they are filled in a 1 mL syringe. In parallel, a calcium chloride solution at a concentration of 30 mg/mL is prepared in an ethanol/water mixture 30/70 (v/v).

For each of the CC solutions, drops are formed by slow ejection of CC through a 27G needle (2 mL). The drops fall in the calcium chloride solution (10 mL), which coagulates them in the form of jellified beads. The beads are left in suspension in the calcium chloride solution for 1 hour, then 80 μL BDDE (BDDE/CC ratio of 1.33 μL/mg) are added. It is left under stirring for 1 hour, then the beads are collected on a filtering membrane. The beads are washed by re-suspending them in water and by filtering them to remove the excess calcium chloride and BDDE which had not reacted. This step is repeated 3 times more, and then the beads are left in suspension in water for 1 hour.

The formation of jellified beads in the calcium chloride solution and during the crosslinking and washing steps is observed. However, after 15 minutes in the last aqueous solution (after 4 washing steps), all the beads are solubilised, whatever the pH of the initial solution. This reveals that the covalent crosslinking of the CC chains of the BDDE has not occurred.

Example 2—Hydrogel Beads Based on Carboxymethyl Chitosan (CC)

This example provides beads of crosslinked CC hydrogel according to the invention, whether spherical (sphericity higher than 0.70), smooth, resistant to compression, with a diameter included between about 20 μm and 400 μm and with a mass water content higher than 85%. It is evaluated whether the beads can be washed in an aqueous medium to purify them and balance them in terms of pH and osmolality. It is also sought to sort the beads according to their diameter.

The beads are produced according to the following general method, with the special conditions and parameters indicated in Table 3. The beads can then be dispersed in a continuous phase and the mix is packaged and possibly sterilised according to the specifications sheet of the target product, for example as described in Example 3. Alternately, the beads can be dried, for example by freeze-drying or any other appropriate drying method, and conditioned in the dry form.

In this example, a solution of CC1 (Table 1) (30 mg/mL) is prepared in a 1% NaOH solution and the BDDE is added in a proportion of 3 μL (0.0162 mmol) per mg CC. This solution is dispersed in droplets using a spray (mini-Büchi) via a binary nozzle with a diameter of 2.8 mm, at an air pressure of 0.3 bar. The droplets fall into a coagulation bath based on calcium chloride (50 mg/mL) in a mixture of water/ethanol 30/70 (v/v), at room temperature, causing their coagulation as spherical beads. The crosslinking step of the CC by the BDDE is then performed, while controlling the temperature and time.

Then the suspension is neutralised by adding a solution of 1N hydrochloric acid, the beads are collected on a filtering membrane under vacuum, they are suspended again in hydrochloric acid, and then collected on the filtering membrane. They are suspended in the saline phosphate buffer, collected by filtration, then this step is renewed until obtaining a suspension of gel beads at the osmolality and at the buffer pH.

Smaller beads are removed, by allowing the higher size beads to settle. Finally, the gel beads are sorted in size by placing them on a sieve with a porosity of 400 μm then by filtration under vacuum with decreasing porosity filters. Thus 3 fractions of hydrogel beads with the references SB2-A, B and C are obtained, which are preserved in suspension in a saline phosphate buffer.

TABLE 3

Preparation of the CC hydrogel beads with references SB2- A, B and C

| Step | | Parameters |
|------|--|-----------|
| Step 1 | Solution of CC and BDDE:<br>Volume: 1 liter<br>[NaOH] = 1%<br>[CC1] = 30 mg/mL<br>[BDDE] = 3 μL (0.016 mmol) per mg polymer | Nozzle: binary (diameter 2.8 mm, Büchi)<br>Flow rate: about 156 mL/h<br>Air pressure: 0.3 bar |
| | Coagulation bath:<br>Volume: 5 liters<br>[CaCl2] = 50 mg/mL<br>Water/ethanol 30/70 v/v | Temperature: room<br>Stirring: 30 minutes |
| Step 2 | Cross-linking | Temperature and duration: 131° C. (5 minutes) then 20° C. for 48 hours |
| Step 3 | Neutralisation of the suspension: [HCl] = 1N | Separation: filtering membrane Number: 2 |
| | Suspension of the beads Buffer: phosphate - pH 7.4 | Separation: filtering membrane Number: up to pH and osmolality of the buffer |
| | Elimination of smaller diameter beads by settling | Elimination of the supernatant, collection of the settled solids |
| Step 4 | Fractioning by size<br>a) Collection of the beads with a diameter lower than 400 μm* by sieving | Sieving by ultrasound<br>Sieve: stainless steel R60.106.000400 (Retsch)<br>Porosity: 400 μm<br>Stirring: ultrasound |
| | b) Filtration of beads issued from step 4a - collection of the fraction >200 μm* (reference SB2-C) | Filtration under vacuum<br>Filter: nylon 200 μm (148147, Spectrum Labs) |
| | b) Filtration of beads issued from step 4b <400 μm - collection of the fraction 100-200 μm* (reference SB2-B) | Filtration under vacuum<br>Filter: nylon 100 μm (148145, Spectrum Labs) |
| | d) Filtration of beads issued from step 4c - collection of the fraction 30-100 μm* (reference SB2-A) | Filtration under vacuum<br>Filter: nylon 30 μm (148136, Spectrum Labs) |
| Step 5 | Phosphate buffer suspension (buffer pH and osmolality: 7.4 and 275 mOsm/kg) | Temperature: 2-8° C. |

*theoretical diameter corresponding to filter porosity announced

Stable beads are actually obtained following the washing, sorting and suspension steps. The 3 fractions of beads are characterised according to the methods such as detailed in the description: size distribution by laser diffractometry (Mastersizer 2000, Malvern); water content using a humidity scale (Moisture Analyzer MA37, Sartorius); compression strength by a qualitative method (with a weight of mass 50 g); sphericity and visual inspection by optical microscopy; surface roughness by scanning confocal microscopy. The results are reported in Table 4.

TABLE 4

| Characteristics of the CC hydrogel beads reference SB2- A, B and C | | | |
|---|---|---|---|
| Reference | SB2-A | SB2-B | SB2-C |
| Size distribution (diameter) | Daverage = 91 µm D(0.1) = 23 µm D(0.5) = 87 µm D(0.9) = 175 µm | Daverage = 197 µm D(0.1) = 97 µm D(0.5) = 194 µm D(0.9) = 310 µm | Daverage = 373 µm D(0.1) = 219 µm D(0.5) = 363 µm D(0.9) = 561 µm |
| Water content % humid mass | 90% | 90% | 90% |
| Visual inspection | Homogenous hydrogel | Homogenous hydrogel | Homogenous hydrogel |
| Ash content (% dry mass) | ND | ND | 17% |
| Compression strength | Yes | Yes | Yes |
| Sphericity | 0.88 | 0.88 | ND* |
| Roughness | Smooth | Smooth | Smooth |
| Insoluble | Absence | Absence | Absence |

*ND: not measured

This bead preparation method allows CC hydrogel beads to be obtained in accordance with the characteristics sought for the invention. In addition, these hydrogel beads withstand the aqueous medium washing steps, which removes excess substances, particularly calcium chloride and BDDE, and balances their medium in terms of pH and osmolality, as checked from the formulations of these beads in Example 3.

Example 3—Preparation of Sterile Formulations Based on CC Hydrogel Beads

The fractions of CC hydrogel beads reference SB2-A or SB2-B in Example 2 are collected and then mixed with a solution of sodium hyaluronate (reference HA2 in Table 2) at 2% (m/m) in a saline phosphate buffer, in a mass proportion of 70/30 in order to obtain to separate formulations. The final pH target is 7.2±0.2 and a final osmolality of 315±35 mOsm/kg.

The formulations are stirred slowly for about 12 hours at room temperature. They are then packaged in 1 mL glass syringes (Hypak, BD), closed with a stopper (Hypak, BD). The syringes are transferred into an autoclave (Systec, DX65). Sterile syringes are then obtained with two formulations of CC hydrogel beads ready for delivery by injection (references FSB1-A and FSB1-B).

The final formulations are characterised (pH, osmolality, residual BDDE content, elastic modulus G', ease of ejection of the composition through a 27G thin needle (TSK, ½"). The beads are then collected to check that they have not been altered by the process (shape, surface, compression strength).

The characteristics of the beads and compositions are indicated in Table 5. For information, the characteristics of the two commercial products are reported in the cutaneous volumisation indication for cosmetic purposes: Restylane LYFT (Galderma) and Ellansé-M (Sinclair Pharma).

TABLE 5

| Characterisation of sterile formulations based on CC hydrogel beads and two commercial products in the indication of cutaneous volumisation | | | | |
|---|---|---|---|---|
| Reference | FSB2-A | FSB2-B | Restylane LYFT | Ellanse-M |
| Beads (mean volume diameter) | SB1-A (90 µm) | SB1-B (200 µm) | approx. 750-1000 µm* | approx. 25-50 µm* |
| Content in BDDE and by-product of BDDE by LC-MS | <2 ppm | <2 ppm | NA | NA |
| pH | 7.15 | 7.25 | ND | ND |
| Osmolality mOsm/kg | 320 | 316 | ND | ND |
| Visual inspection | Homogenous | Homogenous | ND | ND |
| Bead shape (optical microscopy) | Spherical | Spherical | Non-spherical | Spherical |
| Surface roughness | Smooth | Smooth | Roughness | Smooth |
| Manual strength of the beads | Resistant | Resistant | NA | NA |
| Elastic modulus G' | 6.2 kPa | 7.0 kPa | 0.7 kPa | 1.1 kPa |
| Average ejection force via a 27G needle (N) | 9 N | 11 N | 10 N | 14 N |

TABLE 5-continued

Characterisation of sterile formulations based on CC hydrogel beads and
two commercial products in the indication of cutaneous volumisation

| Reference | FSB2-A | FSB2-B | Restylane LYFT | Ellanse-M |
|---|---|---|---|---|
| Visual inspection of the beads after ejection via 27G needle (by optical microscopy) | Integral | Integral | NA | Integral |

ND: non-measured;
NA: non-applicable;
*according to literature.

It is concluded from this example that the CC hydrogel beads according to the invention may be formulated kin a solution of HA, then packaged and sterilised in a 1 mL syringe without being altered, as they maintain their homogeneity, their spherical shape, their smooth surface and their compression strength.

The two formulations FSB2-A and B are compliant in terms of pH balance and osmolality with the aqueous phase used. They are compliant in terms of residual content in BDDE and by-product of the BDDE (<2 ppm).

The formulations are easily injectable via a 27G needle, requiring a force of 9 to 10N for their ejection in the air, fully satisfactory particularly for a hypodermal injection. The beads maintain their integrity after ejection, as checked by visual inspection using optical microscopy. Therefore the formulations would be adapted to an indication of cutaneous volumisation for cosmetic purposes, particularly by injection in the hypodermis.

The elastic modulus of these two bead formulations SB2-a and B is significantly higher than that of reference commercial products, and this by virtue of the beads themselves and not the phase in which they are suspended. Indeed, a non-crosslinked HA solution without beads is known to have a value of G' significantly lower. This high elasticity of the beads is advantageous for tissue volumisation indications, as they could be deformed during tissue movements without being compacted or losing their volumising capacity.

Example 4—CC and HA Hydrogel Beads with a Variable Composition

In this example, it is sought to modulate the properties of the CC hydrogel beads while maintaining their manual compression strength, their smooth surface and their sphericity. To achieve this, hyaluronan is added, in the form of sodium hyaluronate (reference HA1 in Table 2) to a CC solution (reference CC2 in Table 1) and BDDE. Two different CC/HA mass ratios are used (50/50 and 75/25) for the same total concentration in polymer of 40 mg/mL. It is sought to form beads with a diameter between 10 μm and 400 μm, approximately. The same general method as in Example 2 is applied, with adjusted parameters as described in Table 6.

TABLE 6

Parameters for the preparation of CC and
HA hydrogel beads reference SB4- A and B

| Step | Parameters | |
|---|---|---|
| Step 1 | Solution of polymers and BDDE: [CC2] + [HA1] = 40 mg/mL Ref SB4-A: CC2/HA1 = 50/50 (m/m) Ref SB4-B: CC2/HA1 = 75/25 (m/m) [NaOH] = 1% [BDDE] = 3 μL (0.016 mmol) per mg polymers Coagulation bath: Volume: 4 liters [CaCl2] = 50 mg/mL Water/ethanol 30/70 v/v | Nozzle: binary (diameter 1.5 mm, Büchi) Pressure on the level of the solution: 1 bar Air pressure: 1 bar Temperature: room Stirring: 30 minutes |
| Step 2 | Cross-linking | Temperature: room Duration: 72 h |
| Step 3 | Neutralisation of the suspension: [HCl] = 1N Purification: washing by saline phosphate buffer (pH 7.4, osmolality 275 mOs/kg) and filtration under vacuum up to pH and osmolality of the buffer | Separation: filtering membrane Filtering membrane 30 μm |
| Step 4 | Collection of fraction >30 μm | Filtering membrane 30 μm |
| Step 5 | Suspension in a solution of HA (reference HA3 in Table 2) at 2% m/m in saline phosphate buffer, with a bead/solution ratio of 70/30 (m/m). Filling in a 1 mL syringe and sterilisation by autoclave. | |

Resistant beads are obtained at the end of the purification, formulation and sterilisation steps. The characteristics of the beads as well as of the final sterile formulations are indicated in Table 7.

TABLE 7

Characteristics of the CC and HA hydrogel beads and bead formulations

| Beads | SB4-A | SB4-B |
|---|---|---|
| CC/HA ratio (m/m) | 50:50 | 75:25 |
| Size distribution* (diameter) | Daverage = 212 μm D(0.1) = 10 μm D(0.5) = 198 μm D(0.9) = 440 μm | ND (observation with an optical microscope indicates a size distribution similar to that of SB2-A) |

TABLE 7-continued

| Characteristics of the CC and HA hydrogel beads and bead formulations | | |
|---|---|---|
| Beads | SB4-A | SB4-B |
| Water content % (m/m) | 97% | 93% |
| Ash content (% dry mass) | 16% | ND |
| Visual inspection | Homogenous | Homogenous |
| Sphericity | ND (observation with an optical microscope confirms that the beads are round) | ND (observation with an optical microscope confirms that the beads are round) |
| Roughness | Smooth | Smooth |
| Manual strength | Resistant (the beads are more reversibly deformable and stickier than the beads in Example 2) | Resistant (the beads are more reversibly deformable and stickier than the beads in Example 2) |
| Formulations | FSB4-A | FSB4-B |
| Elastic modulus G' | 0.27 kPa | 0.64 kPa |
| Ejection force via a 27G needle | 3 N | 4 N |
| Integrity of the beads after ejection | Yes | Yes |

*size measurement by optical microscopy (on 3 images with magnification 4);
ND: not determined CC and HA beads are obtained, with a water content (93% and 97%) increased with respect to the CC beads only in Example 1 (90%). They are more deformable, more elastic and stickier than the beads in Example 1.

It is concluded that the characteristics of CC hydrogel beads can be modulated by changing the composition of the polymer solution, for example by adding HA in variable proportions. The same general method could be applied, with an adaptation of some parameters.

Example 5—Hydrogel Beads Based on CC with a Variable Molecular Structure

In this example, it is sought to form hydrogel beads from a CC of *Agaricus bisporus* origin with a DA lower than 30% (reference CC3 in Table 1), according to the same general method than in Example 2 by adjusting the parameters (Table 8).

By facility, the droplets are formed by passing the polymer solution through a 30G needle instead of the spraying process in Examples 2 to 3. Therefore, the beads will have a diameter higher than those in Examples 1 to 3 (about 1 mm). Nevertheless, this process allows judging compliance of the beads in terms of sphericity, smooth surface and proper resistance to manual compression after the washing steps.

TABLE 8

| Preparation of CC hydrogel beads with a DA lower than 30% | | |
|---|---|---|
| Step | Parameters | |
| Step 1 | Solution of polymer and BDDE: Volume: 2 mL [NaOH] = 1% [CC3] = 20 mg/mL [BDDE] = 1 μL (0.0054 mmol) per mg polymer | Formation of droplets: Needle 30G (½, TSK) Ejection speed: about 1 mL/min |

TABLE 8-continued

| Preparation of CC hydrogel beads with a DA lower than 30% | | |
|---|---|---|
| Step | Parameters | |
| | Coagulation bath: Volume: 100 mL [CaCl2] = 50 mg/mL Water/ethanol = 80/20 v/v | Temperature: room Stirring: 30 minutes |
| Step 2 | Cross-linking | Temperature and time: room temperature for 30 minutes |
| Step 3 | Neutralisation of the suspension: [HCl] = 1N Washing: water Filtration under vacuum Collection of fraction >30 μm | Separation: filtering membrane 30 μm Number: up to pH and osmolality of the buffer |
| Step 4 | Suspension of the beads in water | |

Beads having resisted to the washing and suspension steps in buffer solution are actually obtained. Their characteristics are reported in Table 9.

TABLE 9

| Characteristics of CC hydrogel beads with a DA lower than 30% | |
|---|---|
| Reference | SB5 |
| DA and DS of the CC (mol %) | DA estimated at 27%; DS estimated at 131% |
| Visual inspection | ND (naked eye observation confirms that the beads are homogenous) |
| Sphericity | ND (naked eye observation confirms that beads are round) |
| Roughness | Smooth (naked eye observation) |
| Compression strength | Resistant |

ND: not determined

It is concluded that beads which are spherical, smooth and resistant to manual compression from a carboxymethyl chitosan with a DA lower than 30%, can be formed according to the general method.

Example 6—CC Hydrogel Beads for Volumisation of Cutaneous Tissues in Rats

In this example, the local tolerance and volumising capacity of CC hydrogel beads are evaluated after injection in the hypodermis (subcutaneous) in rats, over a period of 3

The average volume of the relief created by the Restylane® LYFT commercial product is initially of the same magnitude as the other products during the first 2 weeks. And then, it is significantly lower than all times due to its progressive reduction from day 14 and until the end of the study (day 85).

TABLE 10

| Volume of the relief created by the subcutaneous injection of products based on particles in rats (average of 6 per time and standard deviation, in mm³) | | | | | | |
|---|---|---|---|---|---|---|
| Reference | Day 2 | Day 7 | Day 14 | Day 29 | Day 57 | Day 85 |
| FSB2-A | 1340 ± 374 | 1657 ± 132 | 1571 ± 322 | 1740 ± 468 | 1559 ± 416 | 1770 ± 537 |
| FSB2-B | 1265 ± 125 | 1701 ± 138 | 1717 ± 191 | 1809 ± 418 | 1753 ± 346 | 1679 ± 382 |
| Ellansé-M | 1394 ± 218 | 1794 ± 404 | 1980 ± 327 | 1742 ± 345 | 1573 ± 210 | 1624 ± 155 |
| Restylane ® LYFT | 926 ± 212 | 1437 ± 138 | 1723 ± 255 | 1508 ± 255 | 1205 ± 81 | 1103 ± 192 | months. the two formulations based on CC hydrogel beads of Example 3, ready for injection: FSB2-A (average diameter in 90 μm volume) and FSB2-B (average diameter in 200 μm volume) are used.

As a comparison, two commercial injectable products intended for cutaneous volumisation for cosmetic purposes are simultaneously studied: Ellansé-M (Sinclair Pharma), based on solid and non-hydrated microspheres of polycaprolactone in a carboxymethyl cellulose gel; Restylane® LYFT (Galderma), hydrogel of hyaluronic acid crosslinked and extruded in the form of non-spherical particles.

The generic term «particles» is used in this example to designate simultaneously CC hydrogel beads, solid microspheres of polycaprolactone and particles of extruded crosslinked hyaluronic acid particles.

Protocol. Wistar female rats each receive a subcutaneous injection of 200 μL of each product (a total 4 injection sites per animal, 2 on the left flank and 2 on the right flank), using a needle size 27G. Regularly over a period of 3 months, any signs of reaction or skin irritation (erythema, oedema) which would be due to the products tested and a score is allocated to them are evaluated. At each time, the dimensions of the relief created on the level are measured if the cutaneous tissue at each implantation site, and the volume is deduced (height×width×length, in mm³). For each product and on each time, the average volume of the 6 implantation sites is calculated. Table 10 indicates the average volume at times representative of the short-, mid- and long-terms of the study.

Evaluation of local tolerance. The scores of erythema and oedema are zero throughout the first week for the 4 products tested. They remain zero throughout the 3-month observation period. Thus no clinical sign of cutaneous irritation reaction is observed for none of the 4 products tested and their tolerance is considered to be excellent.

Evaluation of the volumising effect. The injection of the 2 products based on CC hydrogel beads causes the presence of an immediate cutaneous relief, the volume of which increase slightly during the first days. The volume stabilises from day 7, maintaining around a stable level during the follow-up period of about 3 months (day 85). These products thus act as expected for a cutaneous volumising. No difference in volume is found between the 2 products.

The volumising effect of the Ellansé-M commercial product is characterised by a high volume relief during the first two weeks, which then stabilises on the same level as those of 2 base products with CC hydrogel beads until the end of the study.

It is concluded for this example that the two products based on CC hydrogel beads of average diameter in 90 μm and 200 μm volume are easily injected in subcutaneous and well tolerated, causing no irritation or inflammation reaction clinically visible during the 3-month period of the study, as expected for an indication of cutaneous volumisation for cosmetic purpose. Their subcutaneous injection allows creating a relief of the cutaneous tissue in a localised manner, constant and extended, as sought.

With an equivalent injected volume, the relief created has a volume relief stable over time, and with a level similar to that created by the Ellansé-M product. It is higher to that created by the Restylane® LYFT product, which decreases gradually over time. The CC hydrogel beads thus confirm their safety and effectiveness as a tissue, more particularly cutaneous, volumisation product.

Example 7—Evaluation of the Local Reaction after Injection of CC Hydrogel Beads in Rats: Histopathological Analysis at 1 and 3 Months In this example, the local reaction is characterised, including inflammatory and with foreign material, of two formulations FSB2-A and B per histopathological analysis of cutaneous tissue on the level of the injection sites of the study in Example 6, at the times of 1 month and 3 months after injection. The tissues of the injection sites of the two reference commercial products are identically operated.

By microscopic observation of the sections of tissue mounted on glass plate and coloured with haematoxylin, different aspects of the local reaction according to the semi-quantitative evaluation system described in the ISO 10993 standard—Part 6 (2016) are evaluated. A score of response is given to each site for each parameter, then the average score is calculated over all the sites. Table 11 reports the results obtained at the two times of 1 and 3 months.

TABLE 11

| Semi-quantitative evaluation of the local response after subcutaneous injection in rats (score according to ISO 10993-6; N = 6 sites per product/time) | | | |
|---|---|---|---|
| | FSB2-A 30-100 μm | FSB2-B 100-200 μm | Ellansé-M | Restylane ® LYFT |
| 1 month Cells | | | | |
| Polymorphonuclear | 0 | 0 | 0 | 0 |
| Lymphocytes | 0.4 ± 0.5 | 0 | 0.7 ± 0.5 | 0 |
| Plasmatic cells | 0 | 0 | 0 | 0 |
| Macrophages | 1 ± 0 | 1 ± 0 | 2.8 ± 0.4 | 1 ± 0 |

TABLE 11-continued

Semi-quantitative evaluation of the local response
after subcutaneous injection in rats (score according
to ISO 10993-6; N = 6 sites per product/time)

| | FSB2-A 30-100 μm | FSB2-B 100-200 μm | Ellansé-M | Restylane ® LYFT |
|---|---|---|---|---|
| Giant cells | 1 ± 0 | 1 ± 0 | 1.8 ± 0.4 | 0 |
| Necrosis | 0 | 0 | 0.3 ± 0.8 | 0 |
| Fibrosis | 1 ± 0 | 1 ± 0 | 2.0 ± 0.0 | 1 |
| Neovascularisation | 1 ± 0 | 1 ± 0 | 1 ± 0 | 1 |
| Encapsulation | 0 | 0 | 0.3 ± 0.8 | 1.2 ± 0.4 |
| Invasion of cells/ fibres in the implanted material | Collagen fibres | Collagen fibres | None | None |
| 3 month | | | | |
| Cells | | | | |
| Polymorphonuclear | 0 | 0.2 ± 0.4 | 0 | 0 |
| Lymphocytes | 0.2 ± 0.4 | 0 | 0.7 ± 0.5 | 0 |
| Plasmatic cells | 0 | 0 | 0 | 0 |
| Macrophages | 1.0 ± 0.0 | 1.0 ± 0.0 | 2.2 ± 0.4 | 1.0 ± 0.0 |
| Giant cells | 0.3 ± 0.5 | 0.5 ± 0.0 | 1.2 ± 0.4 | 0 |
| Necrosis | 0 | 0 | 0 | 0 |
| Fibrosis | 1 | 1.0 ± 0.0 | 1.8 ± 0.4 | 1.0 ± 0.0 |
| Neovascularisation | 1 | 1.0 ± 0.0 | 1.0 ± 0.0 | 1.0 ± 0.0 |
| Encapsulation | 0 | 0 | 0 | 1.0 ± 0.0 |
| Invasion of cells/ fibres in the implanted material | Collagen fibres | Collagen fibres | None | None |

Scores: 0 = no response; 1 = low; 2 = moderate; 3 = marked

At 1 month, the local reaction occurs in an appropriate manner for products based on hydrogel particles (CC beads and Restylane® LYFT), with responses of score «none to low» for all parameters. At 3 months, the cellular response has not increased or decreased, and an invasion of tissue within the CC hydrogel beads (but no Restylane particles) is observed. For the Ellansé-M product, a higher cellular reaction is noted at 1 month, with a «moderate to marked» score for macrophages and scores higher than the other products for lymphocytes and giant cells. The presence of a necrosis is observed for one of the sites. The reaction remains important at 3 months, resulting from a recurrent inflammatory response characterised by the persistence of lymphocytes, macrophages («moderate to marked» score) and giant cells, to scores always higher than for the other products.

It is concluded from this example than the two products based on CC hydrogel beads according to the invention cause an appropriate local reaction at 1 and 3 months after subcutaneous injection. No or little encapsulation of the beads by the cells or a fibrous tissue is observed, but rather the presence of collagen fibres in the material, sign of good biointegration and a minimum risk of granuloma in the long term, as sought by the invention.

Example 8—Incorporation of Ascorbic Acid in CC Hydrogel Beads

In this example, a model molecule (water soluble here), ascorbic acid, in the pre-formed CC hydrogel beads is incorporated in order to demonstrate their ability to act as a tank for substances, for example active ingredients, nutriments, etc. The beads reference SB2-C (average volume diameter 373 μm) of Example 2, collected beforehand under their hydrated form are used. The beads are placed in suspension in a solution of ascorbic acid at a concentration of 50 mg/ml in saline phosphate buffer, then a slight stirring is applied during 12 hours at room temperature. The beads are then separated from the solution by filtration under vacuum on a membrane, and placed in suspension in the saline phosphate buffer for 7 days. A fraction of the beads is characterised by FTIR, after rinsing them by washing with the buffer and dehydrated by freeze-drying.

The same process is applied to the SB2-C beads placed in suspension in the same buffer but without ascorbic acid and their FTIR spectrum is recorded. The FTIR spectrums of the beads placed in suspension in the ascorbic acid solution have two additional bands at 862 $cm^{-1}$ and 530 $cm^{-1}$ with respect to the spectrums of the beads placed in suspension in the buffer alone, which confirms the presence of ascorbic acid in the CC beads.

It is concluded from this example that the CC hydrogel beads are able to act as a tank for a water soluble molecule as ascorbic acid, by incorporating them via a simple diffusion process of ascorbic acid to the pre-formed beads. The fact that ascorbic acid is still present after 7 days in phosphate buffer and washing confirms that the incorporation actually occurs at the heart of the beads, and not only on the surface.

Example 9—Encapsulation of Triamcinolone Hexacetonide into Hydrogel Beads

In view of a local and gradual delivery of triamcinolone, an anti-inflammatory agent of the corticosteroid type, it is sought to encapsulate it into the hydrogel beads. It must be possible to implant or inject the beads in a tissue or an organ.

The encapsulation process allows encapsulating triamcinolone without altering it. The beads contain at least 80% water, are spherical and resistant to compression. Being non-water soluble, triamcinolone is dispersed in the hydrogel of the beads. The triamcinolone powder present in particles of a diameter included between 1 μm and 10 μm, which are thus visible to the naked eye, which is acceptable as a smooth surface and the transparency of the beads are not required for local delivery applications.

Triamcinolone is suspended with the initial solution of the polymer(s) (references CC1 and HA1 of Tables 1 and 2) in the first bead preparation step. Then, the beads are formed according to the general method of Examples 2 and 4, at the beginning of a solution including the polymer(s), triamcinolone and the crosslinking agent (BDDE). The beads are collected, without fractioning them according to their size. The beads are characterised according to the methods described in the previous examples (Table 12).

The triamcinolone content in the beads is evaluated using the following method: An amount of beads is introduced in centrifugation tubes and placed in suspension in an ethanol/water solution (30:20, v/v), ensuring dissolution and diffusion of triamcinolone outside the beads. After 24 hours, the suspension is centrifuged at 2,500 rpm for 10 minutes. Then the absorbance of supernatant is measured at 242 nm using a spectrophotometer (Multiskan Sky High, Thermo Scientific). A calibration curve is produced in the same conditions with solutions of triamcinolone from 0 to 0.5 mg/mL. The triamcinolone content is expressed in mass of triamcinolone per mass of humid beads (Table 12).

TABLE 12

Characteristics of hydrogel and triamcinolone beads

| Reference | SB8-1 | SB8-2 | SB8-3 |
|---|---|---|---|
| Polymer (reference) | CC1 | CC1/HA1 | CC1/HA1 |
| CC/HA ratio (m/m) | (100%) | (50:50) | (75:25) |

TABLE 12-continued

| Characteristics of hydrogel and triamcinolone beads | | | |
|---|---|---|---|
| Reference | SB8-1 | SB8-2 | SB8-3 |
| Average diameter of humid beads (μm) | 305 μm | 443 μm | 207 μm |
| Water content % (m/m) | 91% | 94% | 91% |
| Triamcinolone content (mg/g humid beads) | 15 mg | 7 mg | 15 mg |
| Visual inspection | The triamcinolone particles are visible, dispersed in the hydrogel of the beads | | |
| Sphericity (via optical microscope) | OK | OK | OK |
| Surface roughness | Slightly rough | Slightly rough | Slightly rough |
| Compression strength | Yes | Yes | Yes |

Thus, encapsulating a significant amount of triamcinolone, from 6 to 15 mg according to the CC and HA composition of the beads was successfully performed. It has been checked by FTIR that the structure of the triamcinolone is not altered. The following 2 observations are reported: triamcinolone is incorporated in the form of particles dispersed within the hydrogel of the beads, which makes them opaque. It is also noted that the beads are not smooth but slightly rough, because of the presence of these particles. These two observations are coherent with the solubility profile of triamcinolone. In addition, the beads comply with the invention in terms of water content, sphericity and resistance to compression.

Example 10—Encapsulation of Triamcinolone Out of Sterilised Hydrogel Beads

Sterile formulations are prepared with the 3 types of hydrogel and triamcinolone beads of Example 9. To do this, the beads are suspended in a hyaluronan solution (reference HA2 in Table 2) according to the same general method as Example 3. The formulations are packaged in 3 mL syringes (Hypak, BD) and sterilised by autoclave.

It can be then checked that the triamcinolone can be released out of the beads, by submitting them to mechanical stress by stirring. This evaluation is made on the beads isolated and rinsed from sterile suspension. For each time of the study up to 27 days, a centrifugation tube is reserved and 1 g humid beads, 8 mL of PBS and 3 stainless steel beads of 4.5 mm diameter are placed. The tubes are subjected to orbital stirring (190 rpm), at room temperature, which allows causing a mechanical degradation, via movements miming those of a joint such as the knee for example.

To assess the triamcinolone concentration released in the supernatant at each time, the beads are settled by centrifugation at 600 rpm during 5 minutes. 0.4 mL supernatant is collected and 0.6 mL ethanol are added. Then the absorbance of the solution is measured at 242 nm wavelength using a spectrophotometer (Multiskan Sky High, Thermo Scientific). A calibration curve is produced in parallel in the same operating conditions with triamcinolone only solutions. The triamcinolone concentration in the supernatant is then calculated for each time (each tube). Finally, the total amount of released triamcinolone, expressed in mg per g humid bead (Table 13) is calculated.

TABLE 13

| Kinetics of release of triamcinolone out of the beads | | | |
|---|---|---|---|
| Duration (days) | SB8-1 | SB8-2 | SB8-3 |
| | Mass of triamcinolone released (mg per g humid beads, total) | | |
| 0 | 0.0 | 0.0 | 0.0 |
| 0.5 | 0.1 | 0.0 | 0.0 |
| 1 | 0.2 | 0.1 | 0.1 |
| 2 | 2.3 | 2.5 | 0.1 |
| 4 | 4.4 | 2.4 | 1.0 |
| 7 | 5.6 | 4.4 | 1.8 |
| 10 | 9.4 | 4.6 | 3.3 |
| 11 | 9.9 | 4.9 | 3.8 |
| 17 | 10.5 | 5.4 | 9.0 |
| 22 | 11.2 | 5.6 | 12.4 |
| 27 | 12.0 | 5.9 | 15.0 |

Triamcinolone is actually released out of the beads, in the supernatant, from some time and then gradually throughout the study. In the conditions of this test, the release starts on the second day for the SB8-1 and SB8-2 beads. For the SB8-3 beads, it starts from the seventh day. The major part of the initial triamcinolone content is released on the last day of the test for the 3 types of beads, which indicates there is no blocking of its release in aqueous medium when the beads are set under mechanical stress.

It is concluded that the triamcinolone can be released gradually out of the hydrogel beads of CC or CC/HA set under mechanical stress. In addition, by varying the polymer composition of the beads, we can modulate the time for triggering release and the release kinetics. The polymer composition of the beads can be adjusted according to the release profile of the active agent used and according to the target indication.

The invention claimed is:

1. A method of aesthetic treatment or aesthetic care comprising administering to a human or animal in need thereof, by injection or implantation at a site in need of aesthetic treatment or aesthetic care, a composition comprising a plurality of beads dispersed within an aqueous phase, wherein the plurality of beads comprise a hydrogel matrix, wherein the hydrogel matrix comprises at least one carboxyalkyl chitosan having glucosamine units, N-acetyl-glucosamine units, and glucosamine units substituted with a carboxyalkyl group, said at least one carboxyalkyl chitosan having a degree of substitution with a group of carboxyalkyl greater than 50%, expressed in number of moles of the substituent with respect to the number of moles of total units, wherein the at least one carboxyalkyl chitosan is crosslinked by covalent bonds between chains of the at least one carboxyalkyl chitosan and/or co-crosslinked by covalent bonds with one or more other polymers, and wherein said plurality of beads remain integral in the aqueous phase.

2. The method of claim 1, wherein the aqueous phase comprises one or more polymers.

3. The method of claim 1, wherein the at least one carboxyalkyl chitosan is co-crosslinked by covalent bonds with another polymer.

4. The method of claim 1, wherein the aqueous phase and/or the plurality of beads are in the form of a hydrogel with a pH and osmolality in balance with a physiological medium.

5. The method of claim 1, wherein said at least one carboxyalkyl chitosan has a degree of substitution with a group of carboxyalkyl that is in a range of greater than 50% to 200%, expressed in the number of moles of the substituent with respect to the number of moles of total units.

6. The method of claim 1, wherein the hydrogel matrix further comprises at least one polymer optionally crosslinking on itself by covalent bonds or cross-linked by covalent bonds with said at least one carboxyalkyl chitosan.

7. The method of claim 1, wherein the hydrogel matrix further comprises at least hyaluronan optionally crosslinking on itself by covalent bonds or cross-linked by covalent bonds with said at least one carboxyalkyl chitosan.

8. The method of claim 1, wherein crosslinking is formed by a crosslinking agent forming said covalent bonds.

9. The method of claim 1, wherein the crosslinking agent is selected from the group consisting of crosslinking biopolymers, polysaccharides, 1,4 butanediol diglycidyl ether, 1-bromo-3,4-epoxybutane, 1-bromo-4,5-epoxypentane, 1-chloro-2,3-epithio-propane, 1-bromo-2,3-epithiopropane, 1-bromo-3,4-epithio-butane, 1-bromo-4,5-epithiopentane, 2,3-dibromopropanol, 2,4-dibromobutanol, 2,5-dibromopentanol, 2,3-dibromopro-panethiol, 2,4-dibromobutanethiol, 2,5-dibromopentane-thiol epichlorohydrin, 2,3-dibromopropanol, 1-chloro-2,3-epithiopropane, dimethylaminopropylcarbodiimide, gallic acid, epigallocatechine gallate, curcumin, tannic acid, genipine, diisocyanate compounds, hexamethylene diisocyanate, toluene diisocyanate, and divinyl sulfone.

10. The method of claim 1, wherein said composition is formulated as an injectable suspension, ready for instillation or implantable in humans or animals.

11. The method of claim 1, wherein the plurality of beads further comprises one or more active agents.

12. The method of claim 1, wherein the administering comprises the injection by subcutaneous or intradermal route of said composition.

13. The method of claim 1, wherein said method is for repairing or filling at least one body liquid or tissue requiring a repair or filling.

14. The method of claim 1, wherein said method is for cosmetic medicine, plastic surgery, internal surgery, or dermatology.

15. The method of claim 1 further comprising:
preparing an aqueous solution comprising said at least one carboxyalkyl chitosan, at least one crosslinking agent, and, optionally, the one or more other polymers;
forming droplets of the aqueous solution; and
crosslinking the at least one carboxyalkyl chitosan and the one or more other polymers, if present in the aqueous solution, with the at least one crosslinking agent within the droplets;
thereby preparing said plurality of beads.

16. The method of claim 15, further comprising placing the droplets in the presence of an aqueous phase that optionally comprises an organic solvent.

17. The method of claim 15 further comprising coagulating the droplets, in the presence of at least one coagulation agent before crosslinking them.

18. The method of claim 15 further comprising subjecting the plurality of beads to purification steps by washing and balancing the pH and osmolality in a physiologically acceptable medium.

19. The method of claim 15 further comprising selecting said plurality beads based on their dimensions.

20. The method of claim 15 further comprising associating the plurality of beads with an aqueous phase, a lipophilic phase, a hydrolipidic phase, or another solid phase, optionally comprising one or more polymers.

21. The method of claim 1, wherein said method is for volumization indications of skin tissue for cosmetic purposes and medication delivery indications, by injection.

22. The method of claim 1, wherein said method is for providing a volumizing or remodelling effect of the outline of the face or body.

23. The method of claim 1, wherein said method is a method for treating lipoatrophies.

24. The method of claim 1, wherein said method is a method of treatment or of cosmetic care by filling cutaneous tissue.

25. The method of claim 24, wherein said method comprises a subcutaneous, intradermal, intra-mucosal, or intramuscular injection of said composition.

26. The method of claim 1, wherein said method comprises the treatment of skin by multiple injections by an intradermal route.

27. The method of claim 1, wherein said method is a method of treatment of appearance of skin wrinkles and/or fine lines, or of enhancement of skin appearance with a rejuvenated look.

28. The method of claim 1, wherein said method is for one or more tissues or organs affected by excessive temperature or burn.

29. The method of claim 1, wherein said injection or implantation is for aesthetic or cosmetic purposes subsequent to an accident or a surgical procedure.

30. The method of claim 1, wherein said method comprises the injection or implantation of said composition in a dermal tissue, an epithelial tissue, a conjunctive tissue, a muscular tissue, an adipose tissue, or a nerve tissue.

31. The method of claim 1, wherein said method is for cutaneous volumisation by injection in the dermis or hypodermis.

32. The method of claim 1, wherein said plurality of beads are microbeads or nanobeads.

33. The method of claim 1, wherein said at least one carboxyalkyl chitosan has a degree of acetylation higher than 30% and up to 80%, expressed as the number of moles of N-acetyl groups with respect to the number of moles of total glucosamine units.

34. The method of claim 1, wherein said composition is sterile and comprises said plurality of beads integral in said aqueous phase.

35. The method of claim 1, wherein said composition is formulated as a subcutaneous or intradermal injectable composition or subcutaneous or intradermal implantable composition.

36. The method of claim 1, wherein said plurality of beads have an average volume diameter from 1 $\mu$m to 450 $\mu$m under their hydrated form.

37. The method of claim 1, wherein said plurality of beads have an average diameter from 20 $\mu$m to 450 $\mu$m under their hydrated form.

38. The method of claim 1, wherein said plurality of beads have an average volume diameter from 25 $\mu$m to 250 $\mu$m under their hydrated form.

39. The method of claim 1, wherein said plurality of beads have an average volume diameter between 1 $\mu$m and 20 $\mu$m under their hydrated form.

40. The method of claim 1, wherein said plurality of beads have an average volume diameter lower than 1000 nm.

41. The method of claim 1, wherein said plurality of beads remain integral in the aqueous phase after injection via a 27-gauge needle.

\* \* \* \* \*